(12) United States Patent
Shallom

(10) Patent No.: US 11,727,954 B2
(45) Date of Patent: *Aug. 15, 2023

(54) DIAGNOSTIC TECHNIQUES BASED ON SPEECH-SAMPLE ALIGNMENT

(71) Applicant: Cordio Medical Ltd., Or Yehuda (IL)

(72) Inventor: Ilan D. Shallom, Gedera (IL)

(73) Assignee: CORDIO MEDICAL LTD., Or Yehuda (IL)

( * ) Notice: Subject to any disclaimer, the term of this patent is extended or adjusted under 35 U.S.C. 154(b) by 153 days.

This patent is subject to a terminal disclaimer.

(21) Appl. No.: 17/233,487

(22) Filed: Apr. 18, 2021

(65) Prior Publication Data

US 2021/0256992 A1    Aug. 19, 2021

Related U.S. Application Data

(63) Continuation of application No. 16/299,178, filed on Mar. 12, 2019, now Pat. No. 11,011,188.

(51) Int. Cl.
*G10L 15/00* (2013.01)
*G10L 25/66* (2013.01)
(Continued)

(52) U.S. Cl.
CPC .............. *G10L 25/66* (2013.01); *G10L 15/22* (2013.01); *G10L 15/30* (2013.01)

(58) Field of Classification Search
CPC .............................. A61B 5/4803; G10L 25/66
See application file for complete search history.

(56) References Cited

U.S. PATENT DOCUMENTS

| 6,168,568 B1 | 1/2001 | Gavriely |
| 6,527,729 B1 | 3/2003 | Turcott |
| (Continued) | | |

FOREIGN PATENT DOCUMENTS

| DE | 102015218948 A1 | 3/2017 |
| SE | 508439 C2 | 10/1998 |
| WO | 2019210261 A1 | 10/2019 |

OTHER PUBLICATIONS

Ney, "The Use of a One-Stage Dynamic Programming Algorithm for Connected Word Recognition," IEEE Transactions on Acoustics, Speech, and Signal Processing, vol. ASSP-32, No. 2, pp. 263-271, Apr. 1984.

(Continued)

*Primary Examiner* — Daniel Abebe
(74) *Attorney, Agent, or Firm* — Kligler & Associates Patent Attorneys Ltd

(57) ABSTRACT

A method includes obtaining a first sequence of reference-sample feature vectors that quantify acoustic features of different respective portions of at least one reference speech sample, which was produced by a subject at a first time while a physiological state of the subject was known, and a second sequence of test-sample feature vectors that quantify the acoustic features of different respective portions of at least one test speech sample, which was produced by the subject at a second time while the physiological state of the subject was unknown. The test-sample feature vectors are mapped to respective ones of the reference-sample feature vectors, under predefined constraints, such that a total distance between the test-sample feature vectors and the respective ones of the reference-sample feature vectors is minimized. In response to the mapping, an output indicating the physiological state of the subject at the second time is generated.

20 Claims, 5 Drawing Sheets

(51) Int. Cl.
    G10L 15/30    (2013.01)
    G10L 15/22    (2006.01)

(56) References Cited

U.S. PATENT DOCUMENTS

| | | | |
|---|---|---|---|
| 9,153,231 | B1 | 6/2015 | Salvador et al. |
| 10,311,980 | B2* | 6/2019 | Kim ................. G16H 10/20 |
| 10,796,205 | B2 | 10/2020 | Shi et al. |
| 10,896,765 | B2* | 1/2021 | Kim ................. G16H 80/00 |
| 2004/0097822 | A1 | 5/2004 | Muz et al. |
| 2005/0038635 | A1 | 2/2005 | Klefenz et al. |
| 2005/0060153 | A1 | 3/2005 | Gable et al. |
| 2007/0100623 | A1 | 5/2007 | Hentschel et al. |
| 2012/0220899 | A1 | 8/2012 | Oh et al. |
| 2013/0166279 | A1 | 6/2013 | Dines et al. |
| 2016/0249842 | A1 | 9/2016 | Ohana Lubelchick |
| 2017/0325779 | A1 | 11/2017 | Spina et al. |
| 2019/0221317 | A1 | 7/2019 | Kempanna et al. |
| 2019/0311815 | A1* | 10/2019 | Kim ................. A61B 5/4088 |
| 2020/0152226 | A1 | 5/2020 | Anushiravani et al. |
| 2020/0168230 | A1 | 5/2020 | Roh et al. |
| 2021/0110894 | A1* | 4/2021 | Shriberg ........... G16H 50/50 |

OTHER PUBLICATIONS

International Application # PCT/IB2020/054952 Search Report dated Sep. 19, 2021.
AU Application # 2019356224 Office Action dated Oct. 21, 2021.
EP Application # 20158069.3 Office Action dated Nov. 17, 2021.
Wikipedia, "Breathing," pp. 1-13, last edited Oct. 17, 2021, as downloaded from https://en.wikipedia.org/wiki/Breathing.
"Sound Speed in Gases," Sound and Hearing, HyperPhysics, Department of Physics and Astronomy, Georgia State University, USA, pp. 1-3, year 2017, as downloaded from http://hyperphysics.phy-astr.gsu.edu/hbase/Sound/souspe3.html.
"Echo Devices," Amazon.com, Inc, Interest-Based Ads, pp. 1-6, year 2021, as downloaded from https://www.amazon.com/echo-devices/s?k=echo+devices.
"The Best Google Home Speakers in 2021," Tom's Guide, Future US Inc., pp. 1-21, year 2021, as downloaded from https://www.tomsguide.com/best-picks/best-google-home-speakers.
West et al., "Measurements of Pulmonary Gas Exchange Efficiency using Expired Gas and Oximetry: Results in Normal Subjects," American Journal of Physiology—Lung Cellular and Molecular Physiology, vol. 314, No. 4, pp. L686-L689, year 2018.
West et al., "A New Method for Noninvasive Measurement of Pulmonary Gas Exchange Using Expired Gas," Respiratory Physiology & Neurobiology, vol. 247, pp. 112-115, year 2018.
Huang et al., "An Accurate Air Temperature Measurement System Based on an Envelope Pulsed Ultrasonic Time-of-Flight Technique," Review of Scientific Instruments, vol. 78, pp. 115102-1-115102-9, year 2007.
Jedrusyna, "An Ultrasonic Air Temperature Meter", Book "Recent Advances in Mechatronics", Springer, Berlin, Heidelberg, pp. 85-89, year 2010.
Cramer, "The Variation of the Specific Heat Ratio and the Speed of Sound in Air with Temperature, Pressure, Humidity, and CO2 Concentration," Journal of the Acoustical Society of America, vol. 93, No. 5, pp. 2510-2516, May 1993.
AU Application # 2020235966 Office Action dated Jun. 30, 2022.
AU Appliation # 2020234072 Office Action dated Aug. 25, 2022.
U.S. Appl. No. 17/074,653 Office Action dated Sep. 2, 2022.
Rao et al., "Acoustic Methods for Pulmonary Diagnosis," HHS Public Access, Author manuscript, pp. 1-39, year 2020 (final version published in IEEE Reviews in Biomedical Engineering, vol. 12, pp. 221-239, year 2019).
International Application # PCT/IB2021/051459 Search Report dated May 25, 2021.
EP Application # 21158827.2 Search Report dated Jul. 28, 2021.
Cohen, "Signal processing methods for upper airway and pulmonary dysfunction diagnosis," IEEE Engineering in Medicine and Biology Magazine, vol. 9, No. 1, pp. 72-75, Mar. 1, 1990.
AU Application # 2019356224 Office Action dated Jan. 17, 2022.
U.S. Appl. No. 16/914,524 Office Action dated Jan. 26, 2022.
International Application # PCT/IB2021/054952 Search Report dated Jan. 30, 2022.
U.S. Appl. No. 16/807,178 Office Action dated Feb. 24, 2022.
Gupta et al., "Characterizing Exhaled Airflow from Breathing and Talking," Indoor Air, vol. 20, pp. 31-39, year 2010.
U.S. Appl. No. 17/074,653 Office Action dated Mar. 9, 2022.
Bhagya et al., "Speed of Sound-Based Capnographic Sensor with Second-Generation CNN for Automated Classification of Cardiorespiratory Abnormalities," IEEE Sensors Journal, vol. 19, issue 19, pp. 8887-8894, Oct. 1, 2019.
Mirza et al., "Analytical Modeling and Simulation of a CMOS-MEMS Cantilever Based CO2 Sensor for Medical Applications," Proceedings IEEE Regional Symposium on Micro and Nanoelectronics, pp. 70-73, Sep. 27, 2013.
International Application # PCT/IB2021/060800 Search Report dated Mar. 21, 2022.
IN Application # 202147045402 Office Action dated Mar. 14, 2022.
EP Application # 21209891.7 Search Report dated Apr. 13, 2022.
IN Application # 202147045344 Office Action dated Apr. 1, 2022.
Eden et al., "Measuring phonological distance between languages", Doctor Thesis, UCL Department of Linguistics, pp. 1-254, year 2018.
Falkhausen et al., "Calculation of Distance Measures Between Hidden Markov Models", 4th European Conference on Speech Communication and Technology, pp. 1487-1490, Sep. 18-21, 1995.
Kempton et al., "Cross-language phone recognition when the target language phoneme inventory is not known", 12th Annual Conference of the International Speech Communication Association, pp. 3165-3168, Aug. 27-31, 2011.
Kienappel et al., "Cross-Language Transfer of Multilingual Phoneme Models", ASR2000-Automatic Speech Recognition Challenges for the New Millennium, pp. 1-5, Sep. 18-20, 2000.
Kohler, "Multi-Lingual Phoneme Recognition Exploiting Acoustic-Phonetic Similarities of Sounds", 4th International Conference on Spoken Language Processing (ICSLP 96), pp. 1-4, Oct. 3-6, 1996.
Pitts et al., "Using Voluntary Cough to Detect Penetration and Aspiration During Oropharyngeal Swallowing in Patients With Parkinson Disease", Chest, vol. 138, issue 6, pp. 1426-1431, Dec. 2010.
Sooful et al., "An acoustic distance measure for automatic cross-language phoneme mapping", PRASA proceedings, pp. 1-4, year 2001.
Sooful et al., "Comparison of acoustic distance measures for automatic cross-language phoneme mapping", 7th International Conference on Spoken Language Processing, pp. 1-4, Sep. 16-20, 2002.
Sterling et al., "Automated Cough Assessment on a Mobile Platform", Journal of Medical Engineering, pp. 1-10, year 2014.
Vaswani et al., "Attention is all you need", 31st Conference on Neural Information Processing systems, pp. 1-11, year 2017.
Zeng et al., "A new distance measure for hidden Markov models", Expert Systems with Applications, vol. 37, pp. 1550-1555, year 2010.
Rabiner et al., "Fundamentals of Speech Recognition", Prentice Hall, chapters 7-8, pp. 390-481, year 1993.
EP Application # 20158058.6 Summons to Oral Proceedings dated Apr. 19, 2023.
EP Application # 19201720.0 Office Action dated Mar. 30, 2023.
EP Application # 21209891.7 Office Action dated May 19, 2023.
JP Application # 2021-517971 Office Action dated May 16, 2023.
Indian Application # 202247066856 Office Action dated Mar. 29, 2023.
Sakran et al., "A Review: Automatic Speech Segmentation", International Journal of Computer Science and Mobile computing (IJCSMC), vol. 6, issue 4, pp. 308-315, Apr. 2017.

* cited by examiner

DIAGNOSTIC TECHNIQUES BASED ON SPEECH-SAMPLE ALIGNMENT

CROSS-REFERENCE TO RELATED APPLICATION

The present application is a continuation of allowed U.S. application Ser. No. 16/299,178, published as US Patent Application Publication 2020/0294531, whose disclosure is incorporated herein by reference.

FIELD OF THE INVENTION

The present invention relates generally to medical diagnostics, particularly with respect to physiological conditions that affect a subject's speech.

BACKGROUND

Sakoe and Chiba, "Dynamic Programming Algorithm Optimization for Spoken Word Recognition," IEEE Transactions on Acoustics, Speech, and Signal Processing 26.2 (1978): 43-49, which is incorporated herein by reference, reports on an optimum dynamic programming (DP) based time-normalization algorithm for spoken word recognition. First, a general principle of time-normalization is given using a time-warping function. Then, two time-normalized distance definitions, called symmetric and asymmetric forms, are derived from the principle. These two forms are compared with each other through theoretical discussions and experimental studies. The symmetric form algorithm superiority is established. A technique, called slope constraint, is introduced, in which the warping function slope is restricted so as to improve discrimination between words in different categories.

Rabiner, Lawrence R., "A tutorial on hidden Markov models and selected applications in speech recognition," Proceedings of the IEEE 77.2 (1989): 257-286, which is incorporated herein by reference, reviews theoretical aspects of types of statistical modeling, and shows how they have been applied to selected problems in machine recognition of speech.

U.S. Pat. No. 7,457,753 describes a system for remote assessment of a user. The system comprises application software resident on a server and arranged to interact across a network with a user operating a client device to obtain one or more sample signals of the user's speech. A datastore is arranged to store the user speech samples in association with details of the user. A feature extraction engine is arranged to extract one or more first features from respective speech samples. A comparator is arranged to compare the first features extracted from a speech sample with second features extracted from one or more reference samples and to provide a measure of any differences between the first and second features for assessment of the user.

US Patent Application Publication 2009/0099848 describes a system and method for passive diagnosis of dementias. Clinical and psychometric indicators of dementias are automatically identified by longitudinal statistical measurements, and mathematical methods are used to track the nature of language change and/or patient audio features. The disclosed system and method include multi-layer processing units wherein initial processing of the recorded audio data is processed in a local unit. Processed and required raw data is also transferred to a central unit which performs in-depth analysis of the audio data.

US Patent Application Publication 2015/0216448 to Lotan et al. describes a method for measuring a user's lung capacity and stamina, to detect Chronic Heart Failure, COPD or Asthma. The method includes providing a client application on the user's mobile communication device, said client application including executable computer code for: instructing the user to fill his lungs with air and utter vocal sounds within a certain range of loudness (decibels) while exhaling; receiving and registering by the mobile communication device said user's vocal sounds; stopping the registering of the vocal sounds; measuring the length of the vocal sounds receiving time within said range of loudness; and displaying the length on the mobile communication device screen.

SUMMARY OF THE INVENTION

There is provided, in accordance with some embodiments of the present invention, a method that includes obtaining at least one speech model constructed from one or more reference speech samples, which were produced by a subject at a first time while a physiological state of the subject was known. The speech model includes (i) one or more acoustic states exhibited in the reference speech samples, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The method further includes receiving at least one test speech sample that was produced by the subject at a second time, while the physiological state of the subject was unknown, and computing a plurality of test-sample feature vectors that quantify acoustic features of different respective portions of the test speech sample. The method further includes, based on the local distance functions and on the allowed transitions, mapping the test speech sample to a minimum-distance sequence of the acoustic states, by mapping the test-sample feature vectors to respective ones of the acoustic states such that a total distance between the test-sample feature vectors and the respective ones of the acoustic states is minimized, the total distance being based on respective local distances between the test-sample feature vectors and the respective ones of the acoustic states. The method further includes, in response to mapping the test speech sample to the minimum-distance sequence of the acoustic states, generating an output indicating the physiological state of the subject at the second time.

In some embodiments, the method further includes receiving the reference speech samples, and obtaining the speech model includes obtaining the speech model by constructing the speech model from the reference speech samples.

In some embodiments, the total distance is based on a sum of the respective local distances.

In some embodiments, the total distance is the sum of the respective local distances.

In some embodiments,
the sum is a first sum,
the model further defines respective transition distances for the allowed transitions, and the total distance is a second sum of (i) the first sum, and (ii) the transition distances for those of the allowed transitions that are included in the minimum-distance sequence of the acoustic states.

In some embodiments, generating the output includes:
comparing the total distance to a predetermined threshold; and
generating the output in response to the comparison.

In some embodiments, the local distance function of each acoustic state returns a value that depends on a negative log of an estimated likelihood that the given acoustic feature vector corresponds to the acoustic state.

In some embodiments, the reference speech samples were produced while the physiological state of the subject was stable with respect to a particular physiological condition.

In some embodiments,
the reference speech samples are first reference speech samples, the speech model is a first speech model, the acoustic states are first acoustic states, the minimum-distance sequence is a first minimum-distance sequence, and the total distance is a first total distance, the method further includes:
  receiving one or more second reference speech samples that were produced by the subject while the physiological state of the subject was unstable with respect to the particular physiological condition;
  based on the second reference speech samples, constructing at least one second speech model that includes one or more second acoustic states exhibited in the second reference speech samples;
  mapping the test speech sample to a second minimum-distance sequence of the second acoustic states, by mapping the test-sample feature vectors to respective ones of the second acoustic states such that a second total distance between the test-sample feature vectors and the respective ones of the second acoustic states is minimized; and
  comparing the second total distance to the first total distance, and
  generating the output includes generating the output in response to comparing the second total distance to the first total distance.

In some embodiments, the reference speech samples were produced while the physiological state of the subject was unstable with respect to a particular physiological condition.

In some embodiments, the reference speech samples and the test speech sample include the same predetermined utterance.

In some embodiments,
the reference speech samples include free speech of the subject,
constructing the at least one speech model includes:
identifying multiple different speech units in the free speech,
constructing respective speech-unit models for the identified speech units, and
constructing the at least one speech model by concatenating the speech-unit models, such that the speech model represents a particular concatenation of the identified speech units, and
the test speech sample includes the particular concatenation.

In some embodiments,
the total distance is a first total distance, and
generating the output includes:
computing a second total distance between the test-sample feature vectors and the respective ones of the acoustic states, the second total distance being different from the first total distance; and
generating the output responsively to the second total distance.

In some embodiments, computing the second total distance includes:
weighting the respective local distances by respective weights, at least two of the weights being different from one another;
computing the second total distance by summing the weighted local distances.

In some embodiments, the respective local distances are first respective local distances, and computing the second total distance includes:
modifying the local distance functions of the respective ones of the acoustic states;
using the modified local distance functions, computing second respective local distances between the test-sample feature vectors and the respective ones of the acoustic states; and
computing the second total distance by summing the second local distances.

In some embodiments, modifying the local distance functions includes modifying the local distance functions so as to give greater weight to at least one of the acoustic features than to at least one other one of the acoustic features.

There is further provided, in accordance with some embodiments of the present invention, an apparatus that includes a network interface and a processor. The processor is configured to obtain at least one speech model constructed from one or more reference speech samples, which were produced by a subject at a first time while a physiological state of the subject was known. The speech model includes (i) one or more acoustic states exhibited in the reference speech samples, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The processor is further configured to receive, via the network interface, at least one test speech sample that was produced by the subject at a second time, while the physiological state of the subject was unknown, and to compute a plurality of test-sample feature vectors that quantify acoustic features of different respective portions of the test speech sample. The processor is further configured to, based on the local distance functions and on the allowed transitions, map the test speech sample to a minimum-distance sequence of the acoustic states, by mapping the test-sample feature vectors to respective ones of the acoustic states such that a total distance between the test-sample feature vectors and the respective ones of the acoustic states is minimized, the total distance being based on respective local distances between the test-sample feature vectors and the respective ones of the acoustic states. The processor is further configured to, in response to mapping the test speech sample to the minimum-distance sequence of the acoustic states, generate an output indicating the physiological state of the subject at the second time.

There is further provided, in accordance with some embodiments of the present invention, a system that includes an analog-to-digital (A/D) converter and one or more processors. The processor are configured to cooperatively carry out a process that includes obtaining at least one speech model constructed from one or more reference speech samples, which were produced by a subject at a first time while a physiological state of the subject was known. The speech model includes (i) one or more acoustic states exhibited in the reference speech samples, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The process further includes receiving, via the A/D converter, at least one test speech sample that was produced by the subject at a second time, while the physiological state of the subject was unknown, and computing a plurality of test-sample feature vectors that quantify acoustic features of different respective portions of the test speech sample. The process further includes, based on the local distance functions and on the allowed transitions, mapping the test speech sample to a minimum-distance sequence of the acoustic states, by mapping the test-sample feature vectors to respective ones of the acoustic states such that a total distance between the test-sample feature vectors and the respective ones of the acoustic states is minimized, the total distance being based on respective local distances between the test-sample feature vectors and the respective ones of the acoustic states. The process further includes, in response to mapping the test speech sample to the minimum-distance sequence of the acoustic states, generating an output indicating the physiological state of the subject at the second time.

There is further provided, in accordance with some embodiments of the present invention, a computer software product including a tangible non-transitory computer-readable medium in which program instructions are stored. The instructions, when read by a processor, cause the processor to obtain at least one speech model constructed from one or more reference speech samples, which were produced by a subject at a first time while a physiological state of the subject was known. The speech model includes (i) one or more acoustic states exhibited in the reference speech samples, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The instructions further cause the processor to receive at least one test speech sample that was produced by the subject at a second time, while the physiological state of the subject was unknown, and to compute a plurality of test-sample feature vectors that quantify acoustic features of different respective portions of the test speech sample. The instructions further cause the processor to, based on the local distance functions and on the allowed transitions, map the test speech sample to a minimum-distance sequence of the acoustic states, by mapping the test-sample feature vectors to respective ones of the acoustic states such that a total distance between the test-sample feature vectors and the respective ones of the acoustic states is minimized, the total distance being based on respective local distances between the test-sample feature vectors and the respective ones of the acoustic states. The instructions further cause the processor to, in response to mapping the test speech sample to the minimum-distance sequence of the acoustic states, generate an output indicating the physiological state of the subject at the second time.

There is further provided, in accordance with some embodiments of the present invention, a method that includes obtaining multiple speech models constructed from free speech of a subject, which was produced at a first time while a physiological state of the subject was known. Each of the speech models includes, for a different respective one of multiple different speech units in the free speech, (i) one or more acoustic states exhibited in the speech unit, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The method further includes receiving at least one test speech sample that was produced by the subject at a second time, while the physiological state of the subject was unknown, and identifying, in the test speech sample, one or more test-sample portions that include the identified speech units, respectively. The method further includes mapping the test-sample portions to respective ones of the speech models, by, for each of the test-sample portions, computing a plurality of test-sample feature vectors that quantify acoustic features of different respective portions of the test-sample portions, identifying the speech model that was constructed for the speech unit included in the test-sample portion, and, based on the local distance functions and on the allowed transitions included in the identified speech model, mapping the test-sample portion to the identified speech model, by mapping the test-sample feature vectors to respective ones of the acoustic states included in the identified speech model such that a total distance between the test-sample feature vectors and the respective ones of the acoustic states is minimized, the total distance being based on respective local distances between the test-sample feature vectors and the respective ones of the acoustic states. The method further includes, in response to mapping the test-sample portions to the respective ones of the speech models, generating an output indicating the physiological state of the subject at the second time.

In some embodiments, the method further includes receiving the free speech, and obtaining the speech models includes obtaining the speech models by:
identifying the speech units in the free speech, and
based on the speech units, constructing the speech models.

In some embodiments, the total distance is based on a sum of the respective local distances.

In some embodiments, the test speech sample includes a predetermined utterance that includes at least one of the identified speech units.

In some embodiments, the free speech is reference free speech, and the test speech sample includes test free speech.

There is further provided, in accordance with some embodiments of the present invention, an apparatus that includes a network interface and a processor. The processor is configured to obtain multiple speech models constructed from free speech of a subject, which was produced at a first time while a physiological state of the subject was known. Each of the speech models includes, for a different respective one of multiple different speech units in the free speech, (i) one or more acoustic states exhibited in the speech unit, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The processor is further configured to receive, via the network interface, at least one test speech sample that was produced by the subject at a second time, while the physiological state of the subject was unknown, and to identify, in the test speech sample, one or more test-sample portions that include the identified speech units, respectively. The processor is further configured to map the test-sample portions to respective ones of the speech models, by, for each of the test-sample portions, computing a plurality of test-sample feature vectors that quantify acoustic features of different respective portions of the test-sample portions, identifying the speech model that was constructed for the speech unit included in the test-sample portion, and, based on the local distance functions and on the allowed transitions included in the identified speech model, mapping the test-sample portion to the identified speech model, by mapping the test-sample feature vectors to respective ones of the acoustic states included in the identified speech model such that a total distance between the test-sample feature vectors and the respective ones of the acoustic states is minimized, the total distance being based on respective local distances between the test-sample feature vectors and the respective ones of the acoustic states. The processor is further configured to, in response to mapping the test-sample portions to the respective ones of the speech models, generate an output indicating the physiological state of the subject at the second time.

There is further provided, in accordance with some embodiments of the present invention, a system that includes an analog-to-digital (A/D) converter and one or more processors. The processors are configured to cooperatively carry out a process that includes obtaining multiple speech models constructed from free speech of a subject, which was produced at a first time while a physiological state of the subject was known. Each of the speech models includes, for a different respective one of multiple different speech units in the free speech, (i) one or more acoustic states exhibited in the speech unit, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The process further includes receiving, via the A/D converter, at least one test speech sample that was produced by the subject at a second time, while the physiological state of the subject was unknown, and identifying, in the test speech sample, one or more test-sample portions that include the identified speech units, respectively. The process further includes mapping the test-sample portions to respective ones of the speech models, by, for each of the test-sample portions, computing a plurality of test-sample feature vectors that quantify acoustic features of different respective portions of the test-sample portions, identifying the speech model that was constructed for the speech unit included in the test-sample portion, and, based on the local distance functions and on the allowed transitions included in the identified speech model, mapping the test-sample portion to the identified speech model, by mapping the test-sample feature vectors to respective ones of the acoustic states included in the identified speech model such that a total distance between the test-sample feature vectors and the respective ones of the acoustic states is minimized, the total distance being based on respective local distances between the test-sample feature vectors and the respective ones of the acoustic states. The process further includes, in response to mapping the test-sample portions to the respective ones of the speech models, generating an output indicating the physiological state of the subject at the second time.

There is further provided, in accordance with some embodiments of the present invention, a computer software product including a tangible non-transitory computer-readable medium in which program instructions are stored. The instructions, when read by a processor, cause the processor to obtain multiple speech models constructed from free speech of a subject, which was produced at a first time while a physiological state of the subject was known. Each of the speech models includes, for a different respective one of multiple different speech units in the free speech, (i) one or more acoustic states exhibited in the speech unit, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The instructions further cause the processor to receive at least one test speech sample that was produced by the subject at a second time, while the physiological state of the subject was unknown, and to identify, in the test speech sample, one or more test-sample portions that include the identified speech units, respectively. The instructions further cause the processor to map the test-sample portions to respective ones of the speech models, by, for each of the test-sample portions, computing a plurality of test-sample feature vectors that quantify acoustic features of different respective portions of the test-sample portions, identifying the speech model that was constructed for the speech unit included in the test-sample portion, and, based on the local distance functions and on the allowed transitions included in the identified speech model, mapping the test-sample portion to the identified speech model, by mapping the test-sample feature vectors to respective ones of the acoustic states included in the identified speech model such that a total distance between the test-sample feature vectors and the respective ones of the acoustic states is minimized, the total distance being based on respective local distances between the test-sample feature vectors and the respective ones of the acoustic states. The instructions further cause the processor to, in response to mapping the test-sample portions to the respective ones of the speech models, generate an output indicating the physiological state of the subject at the second time.

There is further provided, in accordance with some embodiments of the present invention, a method that includes obtaining at least one speech model that includes (i) one or more acoustic states exhibited in one or more reference speech samples, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The method further includes receiving at least one test speech sample that was produced by a subject, and computing a plurality of test-sample feature vectors that quantify acoustic features of different respective portions of the test speech sample. The method further includes, based on the local distance functions and on the allowed transitions, mapping the test speech sample to a minimum-distance sequence of the acoustic states, by mapping the test-sample feature vectors to respective ones of the acoustic states such that a first total distance between the test-sample feature vectors and the respective ones of the acoustic states is minimized, the first total distance being based on respective local distances between the test-sample feature vectors and the respective ones of the acoustic states. The method further includes computing a second total distance between the test-sample feature vectors and the respective ones of the acoustic states, the second total distance being different from the first total distance, and, responsively to the second total distance, generating an output indicating a physiological state of the subject.

There is further provided, in accordance with some embodiments of the present invention, an apparatus that includes a network interface and a processor. The processor is configured to obtain at least one speech model that includes (i) one or more acoustic states exhibited in one or more reference speech samples, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The processor is further configured to receive, via the network interface, at least one test speech sample that was produced by a subject, and to compute a plurality of test-sample feature vectors that quantify acoustic features of different respective portions of the test speech sample. The processor is further configured to, based on the local distance functions and on the allowed transitions, map the test speech sample to a minimum-distance sequence of the acoustic states, by mapping the test-sample feature vectors to respective ones of the acoustic states such that a first total distance between the test-sample feature vectors and the respective ones of the acoustic states is minimized, the first total distance being based on respective local distances between the test-sample feature vectors and the respective ones of the acoustic states. The processor is further configured to compute a second total distance between the test-sample feature vectors and the respective ones of the acoustic states, the second total distance being different from the first total distance, and, responsively to the second total distance, generate an output indicating a physiological state of the subject.

There is further provided, in accordance with some embodiments of the present invention, a system that includes an analog-to-digital (A/D) converter and one or more processors. The processors are configured to cooperatively carry out a process that includes obtaining at least one speech model that includes (i) one or more acoustic states exhibited in one or more reference speech samples, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The process further includes receiving, via the A/D converter, at least one test speech sample that was produced by a subject, and computing a plurality of test-sample feature vectors that quantify acoustic features of different respective portions of the test speech sample. The process further includes, based on the local distance functions and on the allowed transitions, mapping the test speech sample to a minimum-distance sequence of the acoustic states, by mapping the test-sample feature vectors to respective ones of the acoustic states such that a first total distance between the test-sample feature vectors and the respective ones of the acoustic states is minimized, the first total distance being based on respective local distances between the test-sample feature vectors and the respective ones of the acoustic states. The process further includes computing a second total distance between the test-sample feature vectors and the respective ones of the acoustic states, the second total distance being different from the first total distance, and, responsively to the second total distance, generating an output indicating a physiological state of the subject.

There is further provided, in accordance with some embodiments of the present invention, a computer software product including a tangible non-transitory computer-readable medium in which program instructions are stored. The instructions, when read by a processor, cause the processor to obtain at least one speech model that includes (i) one or more acoustic states exhibited in one or more reference speech samples, the acoustic states being associated with respective local distance functions such that, given any acoustic feature vector within a domain of the local distance functions, the local distance function of each acoustic state returns a local distance indicating a degree of correspondence between the given acoustic feature vector and the acoustic state, and (ii) provided that the speech model includes multiple acoustic states, allowed transitions between the acoustic states. The instruction further cause the processor to receive at least one test speech sample that was produced by a subject, and to compute a plurality of test-sample feature vectors that quantify acoustic features of different respective portions of the test speech sample. The instruction further cause the processor to, based on the local distance functions and on the allowed transitions, map the test speech sample to a minimum-distance sequence of the acoustic states, by mapping the test-sample feature vectors to respective ones of the acoustic states such that a first total distance between the test-sample feature vectors and the respective ones of the acoustic states is minimized, the first total distance being based on respective local distances between the test-sample feature vectors and the respective ones of the acoustic states. The instruction further cause the processor to compute a second total distance between the test-sample feature vectors and the respective ones of the acoustic states, the second total distance being different from the first total distance, and, responsively to the second total distance, generate an output indicating a physiological state of the subject.

There is further provided, in accordance with some embodiments of the present invention, a method that includes obtaining a plurality of reference-sample feature vectors that quantify acoustic features of different respective portions of at least one reference speech sample, which was produced by a subject at a first time while a physiological state of the subject was known. The method further includes receiving at least one test speech sample that was produced by the subject at a second time, while the physiological state of the subject was unknown, and computing a plurality of test-sample feature vectors that quantify the acoustic features of different respective portions of the test speech sample. The method further includes mapping the test speech sample to the reference speech sample, by mapping the test-sample feature vectors to respective ones of the reference-sample feature vectors, under predefined constraints, such that a total distance between the test-sample feature vectors and the respective ones of the reference-sample feature vectors is minimized. The method further includes, in response to mapping the test speech sample to the reference speech sample, generating an output indicating the physiological state of the subject at the second time.

In some embodiments, the method further includes receiving the reference speech sample, and obtaining the reference-sample feature vectors includes obtaining the reference-sample feature vectors by computing the reference-sample feature vectors based on the reference speech sample.

In some embodiments, the total distance is derived from respective local distances between the test-sample feature vectors and the respective ones of the reference-sample feature vectors.

In some embodiments, the total distance is a weighted sum of the local distances.

In some embodiments, mapping the test speech sample to the reference speech sample includes mapping the test speech sample to the reference speech sample using a dynamic time warping (DTW) algorithm.

In some embodiments, generating the output includes:
comparing the total distance to a predetermined threshold; and
generating the output in response to the comparison.

In some embodiments, the reference speech sample was produced while the physiological state of the subject was stable with respect to a particular physiological condition.

In some embodiments,
the reference speech sample is a first reference speech sample, the reference-sample feature vectors are first reference-sample feature vectors, and the total distance is a first total distance,
the method further includes:
receiving at least one second reference speech sample that was produced by the subject while the physiological state of the subject was unstable with respect to the particular physiological condition;
computing a plurality of second reference-sample feature vectors that quantify the acoustic features of different respective portions of the second reference speech sample;
mapping the test speech sample to the second reference speech sample, by mapping the test-sample feature vectors to respective ones of the second reference-sample feature vectors, under the predefined constraints, such that a second total distance between the test-sample feature vectors and the respective ones of the second reference-sample feature vectors is minimized; and
comparing the second total distance to the first total distance, and
generating the output includes generating the output in response to comparing the second total distance to the first total distance.

In some embodiments, the reference speech samples were produced while the physiological state of the subject was unstable with respect to a particular physiological condition.

In some embodiments, the reference speech sample and the test speech sample include the same predetermined utterance.

In some embodiments, the reference speech sample includes free speech of the subject, and the test speech sample includes a plurality of speech units that are included in the free speech.

In some embodiments,
the total distance is a first total distance, and generating the output includes:
computing a second total distance between the test-sample feature vectors and the respective ones of the reference-sample feature vectors, the second total distance being different from the first total distance; and
generating the output responsively to the second total distance.

In some embodiments,
the first total distance is a first weighted sum of respective local distances between the test-sample feature vectors and the respective ones of the reference-sample feature vectors, in which first weighted sum the local distances are weighted by respective first weights, and
the second total distance is a second weighted sum of the respective local distances in which the local distances are weighted by respective second weights, at least one of the second weights being different from a corresponding one of the first weights.

In some embodiments, the method further includes:
associating the reference-sample feature vectors with respective acoustic phonetic units (APUs); and
selecting the second weights responsively to the APUs.

In some embodiments, associating the reference-sample feature vectors with the APUs includes associating the reference-sample feature vectors with the APUs by applying a speech-recognition algorithm to the reference speech sample.

In some embodiments,
the first total distance is based on respective first local distances between the test-sample feature vectors and the respective ones of the reference-sample feature vectors, and
the second total distance is based on respective second local distances between the test-sample feature vectors and the respective ones of the reference-sample feature vectors, at least one of the second local distances being different from a corresponding one of the first local distances.

In some embodiments,
mapping the test speech sample to the reference speech sample includes computing the first local distances using a first distance measure, and
computing the second total distance includes computing the second local distances using a second distance measure that is different from the first distance measure.

In some embodiments, computing the second total distance includes computing the second local distances based on at least one of the acoustic features that did not contribute to the first local distances.

There is further provided, in accordance with some embodiments of the present invention, an apparatus that includes a network interface and a processor. The processor is configured to obtain a plurality of reference-sample feature vectors that quantify acoustic features of different respective portions of at least one reference speech sample, which was produced by a subject at a first time while a physiological state of the subject was known. The processor is further configured to receive, via the network interface, at least one test speech sample that was produced by the subject at a second time, while the physiological state of the subject was unknown, and to compute a plurality of test-sample feature vectors that quantify the acoustic features of different respective portions of the test speech sample. The processor is further configured to map the test speech sample to the reference speech sample, by mapping the test-sample feature vectors to respective ones of the reference-sample feature vectors, under predefined constraints, such that a total distance between the test-sample feature vectors and the respective ones of the reference-sample feature vectors is minimized. The processor is further configured to, in response to mapping the test speech sample to the reference speech sample, generate an output indicating the physiological state of the subject at the second time.

There is further provided, in accordance with some embodiments of the present invention, a system that includes an analog-to-digital (A/D) converter and one or more processors. The processors are configured to cooperatively carry out a process that includes obtaining a plurality of reference-sample feature vectors that quantify acoustic features of different respective portions of at least one reference speech sample, which was produced by a subject at a first time while a physiological state of the subject was known. The process further includes receiving, via the A/D converter, at least one test speech sample that was produced by the subject at a second time, while the physiological state of the subject was unknown, and computing a plurality of test-sample feature vectors that quantify the acoustic features of different respective portions of the test speech sample. The process further includes mapping the test speech sample to the reference speech sample, by mapping the test-sample feature vectors to respective ones of the reference-sample feature vectors, under predefined constraints, such that a total distance between the test-sample feature vectors and the respective ones of the reference-sample feature vectors is minimized. The process further includes, in response to mapping the test speech sample to the reference speech sample, generating an output indicating the physiological state of the subject at the second time.

There is further provided, in accordance with some embodiments of the present invention, a computer software product including a tangible non-transitory computer-readable medium in which program instructions are stored. The instructions, when read by a processor, cause the processor to obtain a plurality of reference-sample feature vectors that quantify acoustic features of different respective portions of at least one reference speech sample, which was produced by a subject at a first time while a physiological state of the subject was known. The instructions further cause the processor to receive at least one test speech sample that was produced by the subject at a second time, while the physiological state of the subject was unknown, and to compute a plurality of test-sample feature vectors that quantify the acoustic features of different respective portions of the test speech sample. The instructions further cause the processor to map the test speech sample to the reference speech sample, by mapping the test-sample feature vectors to respective ones of the reference-sample feature vectors, under predefined constraints, such that a total distance between the test-sample feature vectors and the respective ones of the reference-sample feature vectors is minimized. The instructions further cause the processor, in response to mapping the test speech sample to the reference speech sample, generate an output indicating the physiological state of the subject at the second time.

The present invention will be more fully understood from the following detailed description of embodiments thereof, taken together with the drawings, in which:

DETAILED DESCRIPTION OF EMBODIMENTS

Overview

Figure 1:
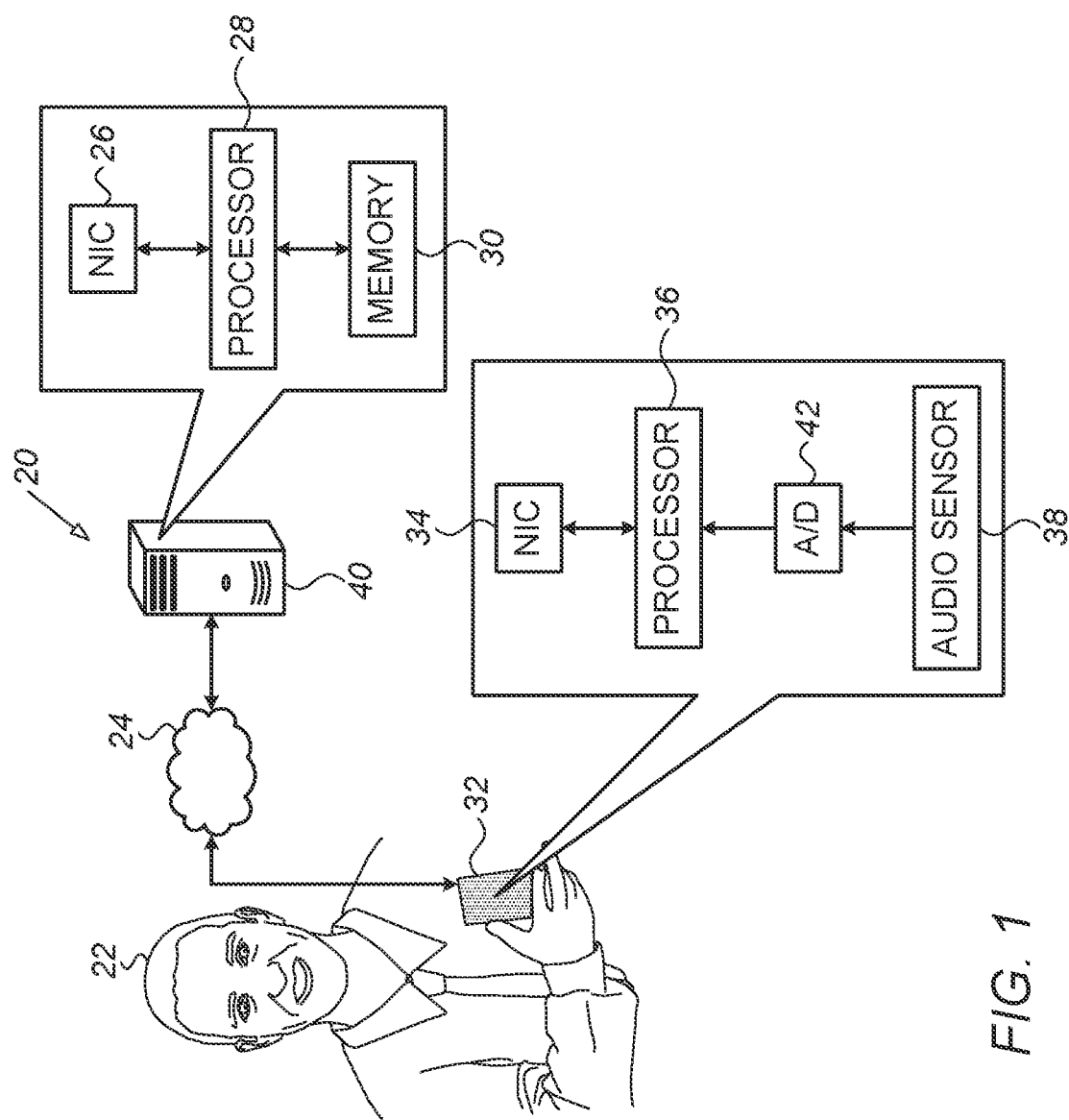
FIG. 1 is a schematic illustration of a system for evaluating the physiological state of a subject, in accordance with some embodiments of the present invention.

Embodiments of the present invention include a system for evaluating the physiological state of a subject by analyzing speech of the subject. For example, by analyzing the subject's speech, the system may identify an onset of, or a deterioration with respect to, a physiological condition such as congestive heart failure (CHF), coronary heart disease, atrial fibrillation or any other type of arrhythmia, chronic obstructive pulmonary disease (COPD), asthma, interstitial lung disease, pulmonary edema, pleural effusion, Parkinson's disease, or depression. In response to the evaluation, the system may generate an output, such as an alert to the subject, to the subject's physician, and/or to a monitoring service.

To evaluate the physiological state of the subject, the system first acquires one or more reference (or "baseline") speech samples from the subject when the physiological state of the subject is deemed to be stable. For example, the reference samples may be acquired following an indication from the subject's physician that the subject's physiological state is stable. As another example, for a subject who suffers from pulmonary edema, the system may acquire the reference speech samples following treatment of the subject to stabilize the subject's breathing. Subsequently to obtaining each reference speech sample, the system extracts a sequence of acoustic feature vectors from the sample. Each feature vector corresponds to a different respective time point in the sample, by virtue of quantifying the acoustic properties of the sample in the temporal vicinity of the time point.

Subsequently to (e.g., several days after) acquiring the reference samples, when the state of the subject is unknown, the system acquires at least one other speech sample from the subject, referred to hereinbelow as a "test speech sample," and extracts respective feature vectors from the sample. Subsequently, based on the feature vectors of the test sample and the reference samples, the system calculates at least one distance value that quantifies the deviation of the test sample from the reference samples, as described in detail below. In response to this distance satisfying one or more predefined criteria (e.g., in response to the distance exceeding a predefined threshold), the system may generate an alert and/or another output.

More particularly, in some embodiments, based on the feature vectors extracted from the reference samples, the system constructs a subject-specific parametric statistical model, which represents the speech of the subject while the subject's physiological state is deemed to be stable. In particular, the subject's speech is represented by multiple acoustic states, which implicitly correspond to respective physical states of the subject's speech-production system. The model further defines the allowed transitions between the states, and may further include respective transition distances (or "costs") for the transitions.

The acoustic states are associated with respective parametric local distance functions, which are defined for a particular domain of vectors. Given any particular feature vector within the domain, each local distance function, when applied to the feature vector, returns a value indicating a degree of correspondence between the feature vector and the acoustic state with which the function is associated. In the present specification, this value is referred to as a "local distance" between the feature vector and the acoustic state.

In some embodiments, each acoustic state is associated with a respective probability density function (PDF), and the local distance between the acoustic state and a feature vector is the negative of the log of the PDF applied to the feature vector. Similarly, each transition may be associated with a respective transition probability, and the cost for the transition may be the negative of the log of the transition probability. At least some models having these properties are known as Hidden Markov Models (HMMs).

Subsequently to constructing the model, to analyze the test speech sample, the system maps the test sample to the model, by assigning each of the test-sample feature vectors (i.e., the feature vectors extracted from the test sample) to a respective one of the acoustic states belonging to the model. In particular, the system selects, from among all possible mappings, the mapping that provides a sequence of states having the minimum total distance, given the allowed state transitions. This total distance may be computed as the sum of the respective local distances between the test-sample feature vectors and the acoustic states to which they are assigned; optionally, the sum of the transition distances included in the sequence may be added to this sum. Responsively to the total distance between the sample and the model, the system may generate an alert and/or another output.

In some embodiments, each of the reference samples includes the same particular utterance, i.e., the same sequence of speech units. For example, the subject's mobile phone may prompt the subject to produce the reference samples by repeating one or more designated sentences, words, or syllables, which may contain any number of designated phonemes, diphones, triphones, and/or other acoustic phonetic units (APUs). As the subject produces the reference samples, a microphone belonging to the mobile phone may record the samples. Subsequently, a processor belonging to the mobile phone or to a remote server may construct, from the samples, a model that represents the particular utterance. Subsequently, to acquire the test sample, the system prompts the subject to repeat the utterance.

In other embodiments, the reference samples are acquired from free speech of the subject. For example, the subject's mobile phone may prompt the subject to answer one or more questions, and the subject's answers to the questions may then be recorded. Alternatively, the subject's speech during a normal conversation may be recorded. Subsequently to acquiring the reference samples, the system uses a suitable speech-recognition algorithm to identify various speech units in the reference samples. For example, the system may identify various words, APUs (such as phonemes, syllables, triphones, or diphones), or synthetic acoustic units such as single HMM states. The system then constructs respective models, referred to herein as "speech-unit models," for these speech units. (In the case of a synthetic acoustic unit that includes a single HMM state, the speech-unit model includes a single-state HMM.)

Subsequently to constructing the speech-unit models, the system may concatenate the speech-unit models into a combined model that represents a particular utterance, based on the order in which the speech units appear in the utterance. (To concatenate any two speech-unit models, the system adds a transition from the final state of one model to the initial state of the other model, and, if transition distances are used, assigns a transition distance to this transition.) The system may then acquire a test sample that includes this particular utterance, and map the test sample to the combined model.

Alternatively, instead of concatenating the speech-unit models, the system may prompt the subject to produce, for the test sample, any particular utterance that includes the speech units for which the speech-unit models were constructed. The system may then identify these speech units in the test sample, and compute the respective "speech-unit distance" between each speech unit and the corresponding speech-unit model. Based on the speech-unit distances, the system may compute a total distance between the test sample and the reference samples. For example, the system may compute the total distance by summing the speech-unit distances.

As yet another alternative, the test sample may be acquired from free speech of the subject. As the system identifies the verbal content of the test sample, the system may compute a respective speech-unit distance for each speech unit in the test sample having a corresponding speech-unit model. The system may then compute the total distance from the speech-unit distances, as described above.

In other embodiments, the system does not construct a model from the reference samples, but rather, directly compares the test speech sample to each of the individual reference samples that were previously acquired. For example, to acquire a reference sample, the system may prompt the subject to utter a particular utterance. Subsequently, to acquire the test sample, the system may prompt the subject to utter the same utterance, and the two samples may then be compared to one another. Alternatively, the system may record free speech of the subject, and extract a reference sample from the free speech, using an automatic speech-recognition (ASR) algorithm to identify the verbal content of the reference sample. Subsequently, to acquire the test sample, the system may prompt the subject to produce the same verbal content.

To perform the comparison between the test and reference samples, the system uses an alignment algorithm, such as the dynamic time warping (DTW) algorithm mentioned above in the Background, to align the test sample with the reference sample, i.e., to find a correspondence between each test-sample feature vector and a respective reference-sample feature vector. (Per the alignment, multiple consecutive test-sample feature vectors may correspond to a single reference-sample feature vector; likewise, multiple consecutive reference-sample feature vectors may correspond to a single test-sample feature vector.) In performing the alignment, the system computes a distance D between the two samples. Subsequently, the system may generate an alert, and/or any other suitable output, responsively to D. (The aforementioned alignment is also referred to below as a "mapping," in that the test sample is mapped to the reference sample.)

In some embodiments, one or more reference speech samples are obtained when the subject's physiological state is deemed to be unstable, e.g., due to the onset of a deterioration with respect to a particular disease. (In the context of the present application, including the claims, the physiological state of a subject is said to be "unstable" if the subject's health is deteriorating in any way, even if the subject does not notice any symptoms of the deterioration.) Based on these samples, the system may construct a parametric statistical model that represents the speech of the subject in the unstable state. The system may then compare the test sample to both the "stable model" and the "unstable model," and generate an alert, for example, if the test sample is closer to the unstable model than to the stable model. Alternatively, even without constructing a stable model, the system may compare the test sample to the unstable model, and generate an alert responsively to the comparison, e.g., in response to the distance between the test sample and the model being less than a predefined threshold.

Similarly, the system may, using an alignment technique as described above, compare the test sample directly to an "unstable" reference sample, alternatively or additionally to comparing the test sample to a "stable" reference sample. Responsively to this comparison, the system may generate an alert.

In some embodiments, multiple reference speech samples are obtained from other subjects, typically while these subjects are in an unstable state with respect to the particular condition from which the subject suffers. Based on these samples (and/or samples that were acquired from the subject), a general (i.e., non-subject-specific) speech model is constructed. Subsequently, the subject's test samples may be mapped to the general model. Advantageously, this technique may obviate the need to acquire a significant number of reference samples from the subject, which may be particularly difficult to do while the subject's state is unstable.

In some embodiments, sequences of reference-sample feature vectors are labeled as corresponding to respective speech units, such as respective words or phonemes. For example, each reference sample may be mapped to a speaker-independent HMM in which groups of one or more states correspond to respective known speech units. (As noted above, such a mapping is in any case performed in the event that the reference sample is obtained from free speech of the subject.) Alternatively, for example, the reference sample may be labeled by an expert. If a model is constructed from the reference samples, the system also labels sequences of states in the model, based on the labeling of the reference samples.

In such embodiments, subsequently to mapping the test sample to the model or to one of the reference samples, the system may recalculate the distance between the test sample and the model or the reference sample, giving greater weight to one or more speech units that are known to be more indicative than others with respect to the particular physiological condition that is being evaluated. The system may then decide whether to generate an alert responsively to the recalculated distance, instead of deciding responsively to the original distance that was computed during the mapping. In recalculating the distance, the system does not change the original mapping, i.e., each test-sample feature vector remains mapped to the same model state or reference-sample feature vector.

Alternatively or additionally, subsequently to mapping the test sample to the model or to one of the reference samples, the system may recalculate the distance between the test sample and the model or the reference sample, using different local distance functions from those that were used for the mapping. In this case, too, the system does not change the original mapping, but rather, only recomputes the distance.

For example, the system may modify the local distance functions to account for one or more features that were not used in performing the mapping, or to give greater weight to certain features. Typically, the features that are emphasized by the system are those that are known to be more indicative than others with respect to the particular physiological condition that is being evaluated. (One example of a more-indicative feature is the variance of the pitch, which tends to decrease with the onset of, or a deterioration with respect to, certain illnesses.) Optionally, the system may also modify the local distance functions such that one or more features have less weight, or do not contribute to the local distance at all.

System Description

Reference is initially made to FIG. 1, which is a schematic illustration of a system 20 for evaluating the physiological state of a subject 22, in accordance with some embodiments of the present invention.

System 20 comprises an audio-receiving device 32, such as a mobile phone, a tablet computer, a laptop computer, a desktop computer, a voice-controlled personal assistant (such as an Amazon Echo™ or Google Home™ device), or a smart speaker device, that is used by subject 22. Device 32 comprises an audio sensor 38 (e.g., a microphone), which converts sound waves to analog electric signals. Device 32 further comprises an analog-to-digital (A/D) converter 42, a processor 36, and a network interface, such as a network interface controller (NIC) 34. Typically, device 32 further comprises a digital memory, a screen (e.g., a touchscreen), and/or other user interface components, such as a keyboard. In some embodiments, audio sensor 38 (and, optionally, A/D converter 42) belong to a unit that is external to device 32. For example, audio sensor 38 may belong to a headset that is connected to device 32 by a wired or wireless connection, such as a Bluetooth connection.

System 20 further comprises a server 40, comprising a processor 28, a digital memory 30, such as a hard drive or flash drive, and a network interface, such as a network interface controller (NIC) 26. Server 40 may further comprise a screen, a keyboard, and/or any other suitable user interface components. Typically, server 40 is located remotely from device 32, e.g., in a control center, and server 40 and device 32 communicate with one another, via their respective network interfaces, over a network 24, which may include a cellular network and/or the Internet.

System 20 is configured to evaluate the subject's physiological state by processing one or more speech signals (also referred to herein as "speech samples") received from the subject, as described in detail below. Typically, processor 36 of device 32 and processor 28 of server 40 cooperatively perform the receiving and processing of at least some of the speech samples. For example, as the subject speaks into device 32, the sound waves of the subject's speech may be converted to an analog signal by audio sensor 38, which may in turn be sampled and digitized by A/D converter 42. (In general, the subject's speech may be sampled at any suitable rate, such as a rate of between 8 and 45 kHz.) The resulting digital speech signal may be received by processor 36. Processor 36 may then communicate the speech signal, via NIC 34, to server 40, such that processor 28 receives the speech signal via NIC 26. Subsequently, processor 28 may process the speech signal.

Typically, in processing the subject's speech, processor 28 compares a test sample, which was produced by the subject while the physiological state of the subject was unknown, to a reference sample, which was produced while the physiological state of the subject was known (e.g., was deemed by a physician to be stable), or to a model constructed from multiple such reference samples. For example, processor 28 may calculate a distance between the test sample and the reference sample or the model.

Based on the processing of the subject's speech samples, processor 28 may generate an output indicating the physiological state of the subject. For example, processor 28 may compare the aforementioned distance to a threshold, and, in response to this comparison, generate an alert, such as an audio or visual alert, indicating a deterioration in the subject's physiological condition. Optionally, such an alert may include a description of the subject's state; for example, the alert may indicate that the subject's lungs are "wet," i.e., partly filled with fluid. Alternatively, if the subject's speech samples indicate that the subject's state is stable, processor 28 may generate an output indicating that the subject's state is stable.

To generate the output, processor 28 may place a call or send a message (e.g., a text message) to the subject, to the subject's physician, and/or to a monitoring center. Alternatively or additionally, processor 28 may communicate the output to processor 36, and processor 36 may then communicate the output to the subject, e.g., by displaying a message on the screen of device 32.

In other embodiments, processor 36 and processor 28 cooperatively perform the aforementioned speech-signal processing. For example, processor 36 may extract vectors of acoustic features from the speech samples (as further described below), and communicate these vectors to processor 28. Processor 28 may then process the vectors as described herein. Alternatively, processor 28 may receive (from processor 36, from one or more other processors, and/or directly) one or more reference speech samples that were produced by subject 22 and/or by one or more other subjects. Based on these samples, processor 28 may compute at least one speech model, or a plurality of reference-sample feature vectors. Processor 28 may then communicate the model, or the reference-sample feature vectors, to processor 36. Based on these data obtained from processor 28, processor 36 may process the test samples from subject 22 as described herein. (Optionally, processor 36 may communicate the aforementioned distance to processor 28. Processor 28 may then compare the distance to the aforementioned threshold and, if appropriate, generate an alert.) As yet another alternative, the entire diagnostic technique described herein may be performed by processor 36, such that system 20 need not necessarily comprise server 40.

Notwithstanding the above, the remainder of the present description, for simplicity, generally assumes that processor 28—also referred to hereinbelow simply as "the processor"—performs all of the processing.

In some embodiments, device 32 comprises an analog telephone that does not comprise an A/D converter or a processor. In such embodiments, device 32 sends the analog audio signal from audio sensor 38 to server 40 over a telephone network. Typically, in the telephone network, the audio signal is digitized, communicated digitally, and then converted back to analog before reaching server 40. Accordingly, server 40 may comprise an A/D converter, which converts the incoming analog audio signal—received via a suitable telephone-network interface—to a digital speech signal. Processor 28 receives the digital speech signal from the A/D converter, and then processes the signal as described herein. Alternatively, server 40 may receive the signal from the telephone network before the signal is converted back to analog, such that the server need not necessarily comprise an A/D converter.

Typically, server 40 is configured to communicate with multiple devices belonging to multiple different subjects, and to process the speech signals of these multiple subjects. Typically, memory 30 stores a database in which data relevant to the speech-sample processing described herein (e.g., one or more reference speech samples or feature vectors extracted therefrom, one or more speech models, and/or one or more threshold distances) are stored for the subjects. Memory 30 may be internal to server 40, as shown in FIG. 1, or external to server 40. For embodiments in which processor 36 processes the subject's speech, a memory belonging to device 32 may store the relevant data for the subject.

Processor 28 may be embodied as a single processor, or as a cooperatively networked or clustered set of processors. For example, a control center may include a plurality of interconnected servers comprising respective processors, which cooperatively perform the techniques described herein. In some embodiments, processor 28 belongs to a virtual machine.

In some embodiments, the functionality of processor 28 and/or of processor 36, as described herein, is implemented solely in hardware, e.g., using one or more Application-Specific Integrated Circuits (ASICs) or Field-Programmable Gate Arrays (FPGAs). In other embodiments, the functionality of processor 28 and of processor 36 is implemented at least partly in software. For example, in some embodiments, processor 28 and/or processor 36 is embodied as a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Constructing a Parametric Statistical Model

Figure 2:
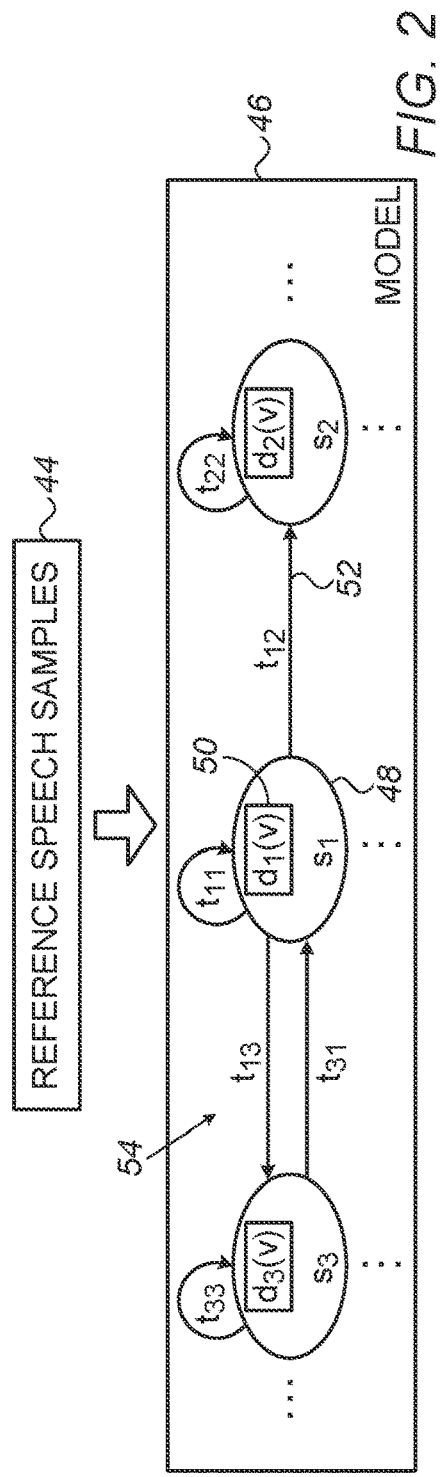
FIG. 2 is a schematic illustration of a construction of a speech model, in accordance with some embodiments of the present invention.

Reference is now made to FIG. 2, which is a schematic illustration of a construction of a speech model 46, in accordance with some embodiments of the present invention.

In some embodiments, processor 28 (FIG. 1) constructs at least one parametric statistical model 46 from one or more reference speech samples 44 that were acquired from subject 22. The processor then uses model 46 to evaluate subsequent speech of the subject.

In particular, the processor first receives samples 44, e.g., via device 32, as described above with reference to FIG. 1. In general, the reference speech samples are produced by the subject while the physiological state of the subject is known. For example, the reference speech samples may be produced while the physiological state of the subject is deemed, by a physician, to be stable with respect to a particular physiological condition. As a particular example, for a subject who suffers from a physiological condition such as pulmonary edema or pleural effusion, the reference samples may be produced while the subject's lungs are deemed to be free from fluid. Alternatively, the reference speech samples may be produced while the physiological state of the subject is unstable with respect to a particular physiological condition, e.g., while the subject's lungs are wet.

Next, based on the received samples, the processor constructs model 46. In particular, the processor typically extracts vectors of acoustic features from the reference samples (as described below with reference to FIG. 3 for the test sample), and then constructs model 46 from the vectors. The model may be stored, for example, in memory 30 (FIG. 1).

Model 46 includes one or more acoustic states 48 (e.g., APUs and/or synthetic acoustic units) that are exhibited in the reference speech samples. Acoustic states 48 are associated with respective local distance functions 50. Given any acoustic feature vector "v" within the domain of functions 50, the local distance function of each acoustic state returns a local distance that indicates a degree of correspondence between the given acoustic feature vector and the acoustic state. Model 46 further includes the transitions 52 between the acoustic states that are exhibited in the reference speech samples; these transitions are referred to herein as "allowed transitions." In some embodiments, model 46 further defines respective transition distances 54 for the transitions.

For example, FIG. 2 shows an example snippet of a speech model, which includes (i) a first acoustic state $s_1$, having a first local distance function $d_1(v)$, (ii) a second acoustic state $s_2$, having a second local distance function $d_2(v)$, and (iii) a third acoustic state $s_3$, having a third local distance function $d_3(v)$. $s_1$ transitions to $s_2$ with a transition distance $t_{12}$, and to $s_3$ with a transition distance $t_{13}$. $s_3$ transitions to $s_1$ with a transition distance $t_{31}$.

As a specific simplified example, if the snippet shown in FIG. 2 represents the word "Bobby" as spoken by the subject in the reference speech samples, $s_1$ may correspond to the phoneme "\b\," s3 may correspond to the phoneme "\aw\," and s2 may correspond to the phoneme "\ee\." (It is noted that typically, in practice, at least some phonemes are represented by a sequence of multiple states.)

In some embodiments, each of the acoustic states is associated with a respective multidimensional probability density function (PDF), from which the local distance between the given feature vector "v" and the acoustic state is implicitly derived. In particular, the PDF provides an estimated likelihood that the given acoustic feature vector corresponds to the acoustic state (i.e., that the given feature vector is derived from speech that was produced while the subject's speech-production system was in the physical state corresponding to the acoustic state), and the local distance is derived from this estimated likelihood. For example, the local distance function of each acoustic state may return a value that depends on the negative log of the estimated likelihood. This value may be, for example, the negative log itself, or a multiple of the negative log.

As a specific example, each acoustic state may be associated with a Gaussian PDF, such that the local distance, when computed as a negative log likelihood, is the sum of the squares of the differences between the components of the feature vector and the corresponding components of the mean of the distribution, weighted by the inverses of the corresponding variances of the distribution.

In other embodiments, the local distances are derived from information-theoretic considerations; one example of a distance measure that is based on such considerations is the Itakura-Saito distance measure, which is mentioned below with reference to FIG. 5. Alternatively, for embodiments in which both a stable model and an unstable model are constructed, the local distances may be derived from class-discrimination considerations, in that the local distances may be selected so as to best discriminate between the stable and unstable reference samples. Alternatively, the local distances may be derived from heuristic considerations.

Typically, transition distances 54 are based on respective transition probabilities, as estimated from the reference speech samples; for example, each transition distance may be the negative log of a respective transition probability.

In general, the parameters of the model (e.g., the parameters of the aforementioned PDFs) and the transition probabilities may be estimated from the reference speech samples using any suitable technique, such as the Baum-Welch algorithm, which is described, for example, in section 6.4.3 of L. Rabiner and B-H. Juang, Fundamentals of Speech Recognition, Prentice Hall, 1993, which is incorporated herein by reference.

Mapping a Test Sample to the Model

Figure 3:
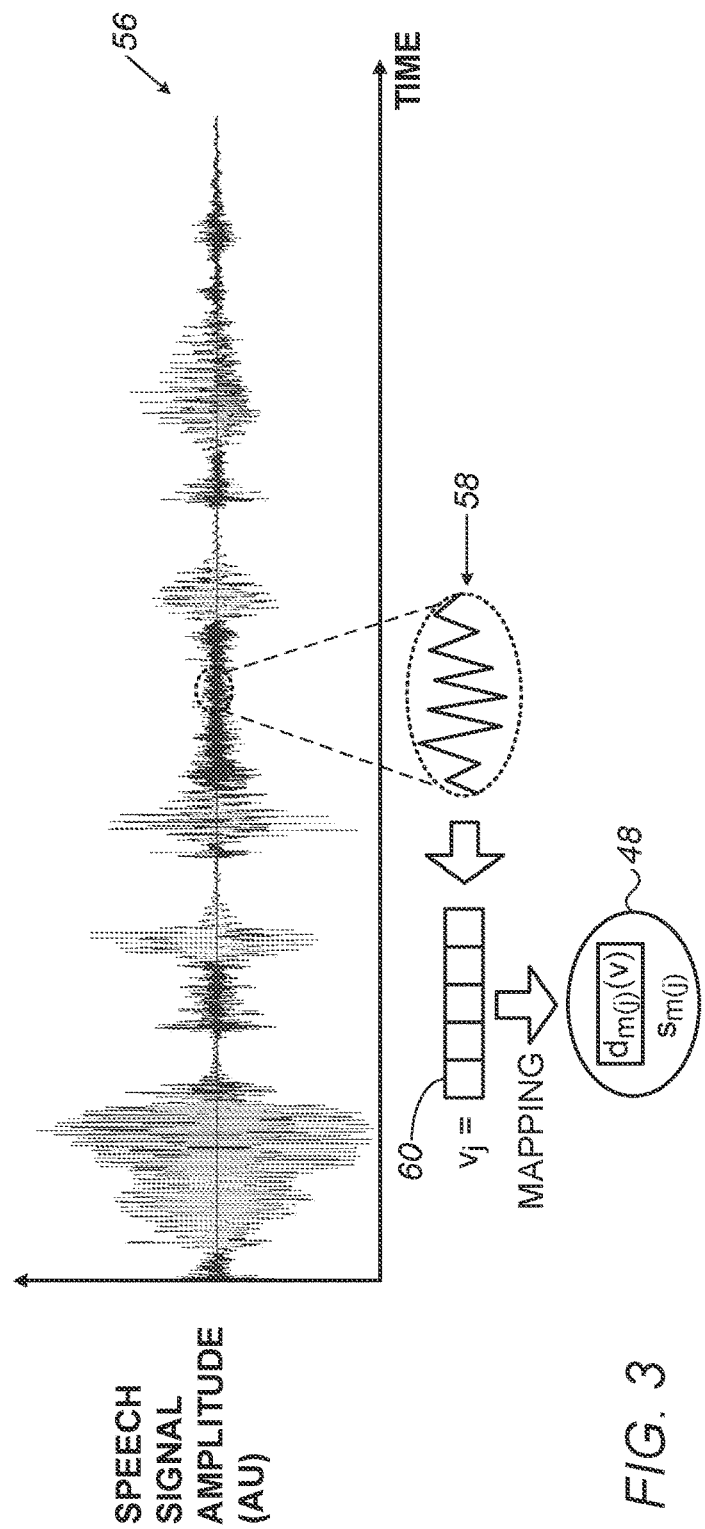
FIG. 3 is a schematic illustration of a mapping of a test speech sample to a speech model, in accordance with some embodiments of the present invention.

Reference is now made to FIG. 3, which is a schematic illustration of a mapping of a test speech sample 56 to a speech model, in accordance with some embodiments of the present invention.

Following the acquisition of the reference samples, at a later time, when the physiological state of the subject is unknown, the processor uses model 46 to assess the physiological state of the subject.

In particular, the processor first receives at least one test speech sample 56 that was produced by the subject while the subject's physiological state was unknown. Next, the processor computes a plurality of test-sample feature vectors 60 that quantify acoustic features of different respective portions 58 of sample 56. The acoustic features may include, for example, a representation of the spectral envelope of portion 58, including, for example, linear prediction coefficients and/or cepstral coefficients. Vectors 60 may include any suitable number of features; by way of example, FIG. 3 shows a five-dimensional vector $v_j$.

In general, each portion 58 may be of any suitable duration, such as, for example, between 10 and 100 ms. (Typically, the portions are of equal duration, although some embodiments may use pitch-synchronous analysis with portions of varying duration.) In some embodiments, portions 58 overlap each other. For example, vectors 60 may correspond to respective time points "t," whereby each vector describes the acoustic features of the portion of the signal occupying the time period [t−T, t+T], where T is, for example, between 5 and 50 ms. Successive time points may be between 10 and 30 ms apart from one another, for example.

Subsequently to computing the feature vectors, based on the local distance functions and on the allowed transitions that are defined by model 46, the processor maps the test speech sample to a minimum-distance sequence of acoustic states belonging to the model, by mapping the test-sample feature vectors to respective ones of the acoustic states such that the total distance between the test-sample feature vectors and the respective ones of the acoustic states is minimized. The total distance is based on the respective local distances between the test-sample feature vectors and the acoustic states to which the feature vectors are mapped; for example, the total distance may be based on the sum of the respective local distances.

To explain further, as illustrated in FIG. 3, each mapping of the test speech sample to the model maps each index "j" of the feature vectors to an index m(j) of the acoustic states, such that the $j^{th}$ feature vector $v_j$ is mapped to the acoustic state $s_{m(j)}$. ($s_{m(j)}$ may be any acoustic state to which there is an allowed transition from $s_{m(j-1)}$.) The mapping of $v_j$ to $s_{m(j)}$ yields a local distance $d_j = d_{m(j)}(v_j)$ between $v_j$ and $s_{m(j)}$. Thus, assuming N test-sample feature vectors, the test sample is mapped to a sequence of N states, and the sum of the local distances for this mapping is $\Sigma_{j=1}^{N} d_j$. The total distance for the mapping is based on $\Sigma_{j=1}^{N} d_j$. For example, the total distance may be defined as $\Sigma_{j=1}^{N} d_j$, or, if transition distances are included in the model, as $\Sigma_{j=1}^{N} d_j + \Sigma_{j=1}^{N-1} t_{j(j+1)}$, where $t_{j(j+1)}$ is the transition distance from the $j^{th}$ state to the $j+1^{st}$ state. The processor finds the sequence of states for which this total distance is minimized.

By way of example, referring again to FIG. 2, and assuming the processor extracts a sequence of six feature vectors $\{v_1, v_2, v_3, v_4, v_5, v_6\}$ from the test sample, the processor may map the test sample to the minimum-distance state sequence $\{s_1, s_3, s_1, s_2, s_2, s_3\}$. The total distance for this mapping may be computed as $d_1(v_1)+t_{13}+d_3(v_2)+t_{31}+d_1(v_3)+t_{12}+d_2(v_4)+t_{22}+d_2(v_5)+t_{23}+d_3(v_6)$.

In some embodiments, to find the optimal mapping of the test sample to the model, the system uses the Viterbi algorithm, which is described in section 6.4.2 of the aforementioned reference to Rabiner and Juang, which is incorporated herein by reference.

Subsequently, in response to mapping the test speech sample to the minimum-distance sequence of acoustic states, the processor generates an output indicating the physiological state of the subject at the time at which the test sample was produced.

For example, the processor may compare the total distance for the optimal mapping to a predetermined threshold, and then generate the output in response to the comparison. In particular, if the reference speech samples were acquired while the subject's state was stable, an alert may be generated in response to the total distance exceeding the threshold; conversely, if the reference speech samples were acquired while the subject's state was unstable, an alert may be generated in response to the total distance being less than the threshold.

In some embodiments, the processor determines the threshold based on the statistical distribution of the total distance over a suitable number of mappings, which may be performed for a single subject (in which case the threshold may be subject-specific), or for multiple respective subjects. In particular, if the mappings are performed when the state of the subject(s) is known to be stable, the threshold may be set such that the total distance is less than the threshold in a sufficiently large percentage (e.g., more than 98%) of the mappings. Conversely, if the mappings are performed when the state of the subject (s) is known to be unstable, the threshold may be set such that the total distance exceeds the threshold in a sufficiently large percentage of the mappings.

Alternatively, the processor may construct two speech models: one using reference speech samples acquired while the subject's state was stable, and another using samples acquired while the subject's state was unstable. The test sample may then be mapped to a respective minimum-distance sequence of states in each of the models. The respective total distances between the test sample and the two models may then be compared to one another, and an output may be generated in response to the comparison. For example, if the distance between the test sample and the stable-state model exceeds the distance between the test sample and the unstable-state model, an alert may be generated.

In some embodiments, the system computes respective total distances, with reference to the same model or to different respective models, for multiple test samples. The system may then generate an alert responsively to the distances, e.g., in response to one or more of the distances exceeding a threshold.

In some embodiments, the reference speech samples and the test speech sample include the same predetermined utterance. For example, to acquire the reference samples, device 32 (FIG. 1) may (e.g., in response to instructions from server 40) prompt the subject to repeatedly utter a particular utterance. Subsequently, to acquire the test sample, the subject may be similarly prompted to utter the same utterance. To prompt the subject, the device may play the utterance, and request (via a written or audio message) that the subject repeat the utterance that was played. Alternatively, for example, the verbal content of the utterance may be displayed on the screen of the device, and the subject may be requested to read the verbal content aloud.

In other embodiments, the reference speech samples include free speech of the subject, i.e., speech whose verbal content was not predetermined by system 20. For example, the reference speech samples may include normal conversational speech of the subject. In this regard, reference is now made to FIG. 4, which is a schematic illustration of a technique for constructing a speech model from multiple speech-unit models 64, in accordance with some embodiments of the present invention.

Figure 4:
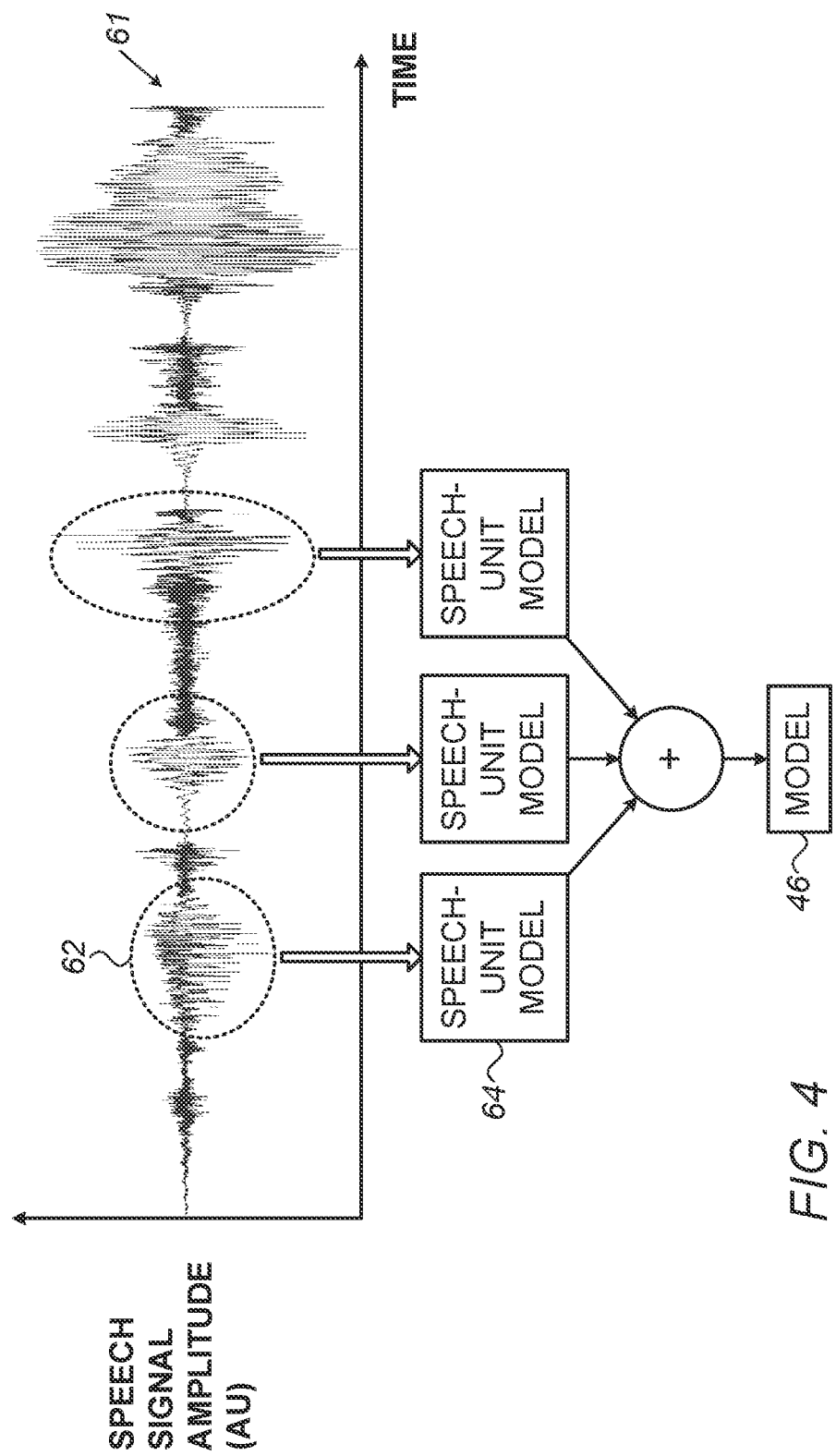
FIG. 4 is a schematic illustration of a technique for constructing a speech model from multiple speech-unit models, in accordance with some embodiments of the present invention.

FIG. 4 depicts a reference sample 61, which includes free speech of the subject. In some embodiments, given such a sample, the processor constructs model 46 by identifying multiple different speech units 62 in the free speech, constructing respective speech-unit models 64 for the identified speech units (as described above with reference to FIG. 2 for model 46), and then constructing model 46 by concatenating speech-unit models 64, such that the speech model represents a particular concatenation of the identified speech units. Each speech unit may include one or more words, APUs, and/or synthetic acoustic units.

For example, assuming that the reference sample includes the sentence "I've been trying all day to reach him, but his line is busy," the processor may identify the speech units "trying," "reach," and "line," and construct respective speech-unit models for these speech units. Subsequently, the processor may construct model 46 by concatenating the speech-unit models, such that, for example, the model represents the utterance "trying reach line."

To identify speech units 62, the processor may use any of the algorithms for speaker-independent, large-vocabulary connected speech recognition described in chapters 7-8 of the aforementioned reference to Rabiner and Juang, which is incorporated herein by reference. One example of such an algorithm is the One Stage Dynamic Programming algorithm, described in Section 7.5 of Rabiner and Juang, and further described in Ney, Hermann, "The use of a one-stage dynamic programming algorithm for connected word recognition," IEEE Transactions on Acoustics, Speech, and Signal Processing 32.2 (1984): 263-271, which is incorporated herein by reference. To identify phonemes or other sub-words, these algorithms may be used in combination with techniques for sub-word recognition, such as those described in Sections 8.2-8.4 of Rabiner and Juang. A language model, described in Sections 8.5-8.7 of Rabiner and Juang, may be used to facilitate this sub-word recognition.

Subsequently, to acquire the test sample, the subject may be prompted to utter the particular utterance that is represented by model 46. For example, continuing the example above, the subject may be prompted to utter "trying reach line."

In other embodiments, the speech-unit models remain separate from each other, i.e., no concatenation is performed. In some such embodiments, the subject is prompted to utter any predetermined utterance that includes at least one of the speech units for which the speech-unit models were constructed. The processor identifies each of those speech units in the utterance, and then processes each speech unit separately. (Typically, the processor identifies each of the speech units using the speech-unit models in combination with a general-speech HMM, which represents all speech aside from the speech units for which the speech-models were constructed.)

In other such embodiments, the processor receives free speech of the subject for the test sample. The processor further identifies, in the test sample, one or more portions that include speech units 62, respectively. For example, if the test sample includes the sentence "Line up, and stop trying to reach the front," the processor may identify the portions of the test sample that include "trying," "reach," and "line." (To identify the verbal content of the test-sample free speech, the processor may use any of the above-described speaker-independent algorithms.)

Subsequently, the processor maps the test-sample portions to respective ones of the speech-unit models, by, for each of the portions, identifying the speech-unit model that was constructed for the speech unit included in the portion, and then performing a minimum-distance mapping of the portion to the corresponding speech-unit model. For example, the processor may map the test-sample portion "trying" to the model that was constructed for the speech unit "trying," "reach" to the model that was constructed for "reach," and "line" to the model that was constructed for "line."

Subsequently, in response to mapping the test-sample portions to the speech-unit models, the processor generates an output indicating the physiological state of the subject. For example, the processor may compute the sum of the respective distances for the mappings, and then generate an output responsively this distance. For example, if the processor calculates the distances $q_1$, $q_2$, and $q_3$ for "trying," "reach," and "line," respectively, the processor may generate an output responsively to $q_1+q_2+q_3$.

Using a Different Total Distance for the Diagnosis

In some embodiments, the processor generates the output not in response to the total distance that was minimized in the mapping, but rather, to a different total distance between the test-sample feature vectors and the respective acoustic states to which the vectors are mapped. In other words, the processor may map the test sample to the model by minimizing a first total distance, but then generate the output in response to a second total distance that is different from the first total distance.

In some embodiments, the processor computes the second total distance by weighting the respective local distances by respective weights, at least two of the weights being different from one another, and then summing the weighted local distances. For example, returning to the example described above with reference to FIG. 2, in which $\{v_1, v_2, v_3, v_4, v_5, v_6\}$ is mapped to $\{s_1, s_3, s_1, s_2, s_2, s_3\}$, the processor may calculate the second total distance as $w_1*d_1(v_1)+t_{13}+w_3*d_3(v_2)+t_{31}+w_1*d_1(v_3)+t_{12}+w_2*d_2(v_4)+t_{22}+w_2*d_2(v_5)+t_{23}+w_3*d_3(v_6)$, where at least two of the weights $\{w_1, w_2, w_3\}$ are different from one another. As a specific example, if the acoustic state $s_1$ has more relevance to the subject's physiological condition than the other two states, $w_1$ may be greater than each of $w_2$ and $w_3$.

Alternatively or additionally, the processor may modify the local distance functions of the respective acoustic states to which the feature vectors are mapped. Using the modified local distance functions, the processor may compute different local distances between the test-sample feature vectors and the respective acoustic states to which the vectors are mapped. The processor may then compute the second total distance by summing these new local distances. For example, for the example mapping described above, the processor may calculate the second total distance as $d'_1(v_1)+t_{13}+d'_3(v_2)+ \ldots +d'_2(v_5)+t_{23}+d'_3(v_6)$, where the notation "d'" indicates a modified local distance function.

Typically, the local distance functions are modified so as to give greater weight to at least one of the acoustic features quantified in the vectors. Typically, the acoustic features selected for greater weighting are those that are known to be more relevant to the subject's physiological condition than other features.

For example, the original local distance function may return, for any given vector $[z_1\ z_2 \ldots z_K]$, the value $\Sigma_{i=1}^{K} b_i$, where $b_i=s_i(z_i-r_i)^2$, where each $r_i$ is a suitable reference quantity, and each $s_i$ is a weight, which may be 0 for some indices. In such embodiments, the modified local distance function may return $\Sigma_{i=1}^{K} c_i$, where $c_i=s'i*(z_i-r_i)^2$, where $\{s'_i\}$ are suitable weights that differ from $s_i$ for at least some of the indices. By using $\{s'_i\}$ that differ from $\{s_i\}$, the processor may adjust the relative weights of the features. In some cases, the modified function may include a non-zero $s'_i$ (and hence, a non-zero $c_i$) for at least one index for which $s_i$ (and hence, $b_i$) is zero, such that the processor, in calculating the second total distance, takes into account at least one feature that was not used at all to perform the mapping. (It is noted that, for efficiency, the actual computation of $\Sigma_{i=1}^{K} b_i$ and of $\Sigma_{i=1}^{K} c_i$ may skip over any zero-valued terms.)

In some embodiments, the subject's test sample is mapped to a non-subject-specific model, which is typically constructed from multiple reference samples produced by other subjects who are unstable with respect to the subject's physiological condition. (Optionally, one or more unstable-state samples from the subject may also be used to construct the model.) Subsequently, a second total distance between the test sample and the model is calculated, as described above. Next, the processor may generate an output responsively to the second total distance. For example, if the model is constructed from unstable-state reference samples as described above, the processor may generate an alert in response to the second total distance being less than a threshold.

Direct Comparison

As noted above in the Overview, in some embodiments, the processor directly compares the test speech sample to a reference sample.

In particular, the processor first receives the reference sample, which, as noted above, is produced by the subject while the physiological state of the subject is known. Subsequently, the processor computes a plurality of reference-sample feature vectors that quantify acoustic features of different respective portions of the reference speech sample, as described above with reference to FIG. 3 for the test sample. These features may be stored in memory 30 (FIG. 1).

Next, at a later time, the processor receives the test sample, which, as noted above, is produced by the subject while the physiological state of the subject is unknown. The processor then extracts test-sample feature vectors from the test sample, as described above with reference to FIG. 3. Subsequently, the processor maps the test speech sample to the reference speech sample, by mapping the test-sample feature vectors to respective ones of the reference-sample feature vectors such that a total distance between the test-sample feature vectors and the respective ones of the reference-sample feature vectors is minimized under predefined constraints.

Figure 5:
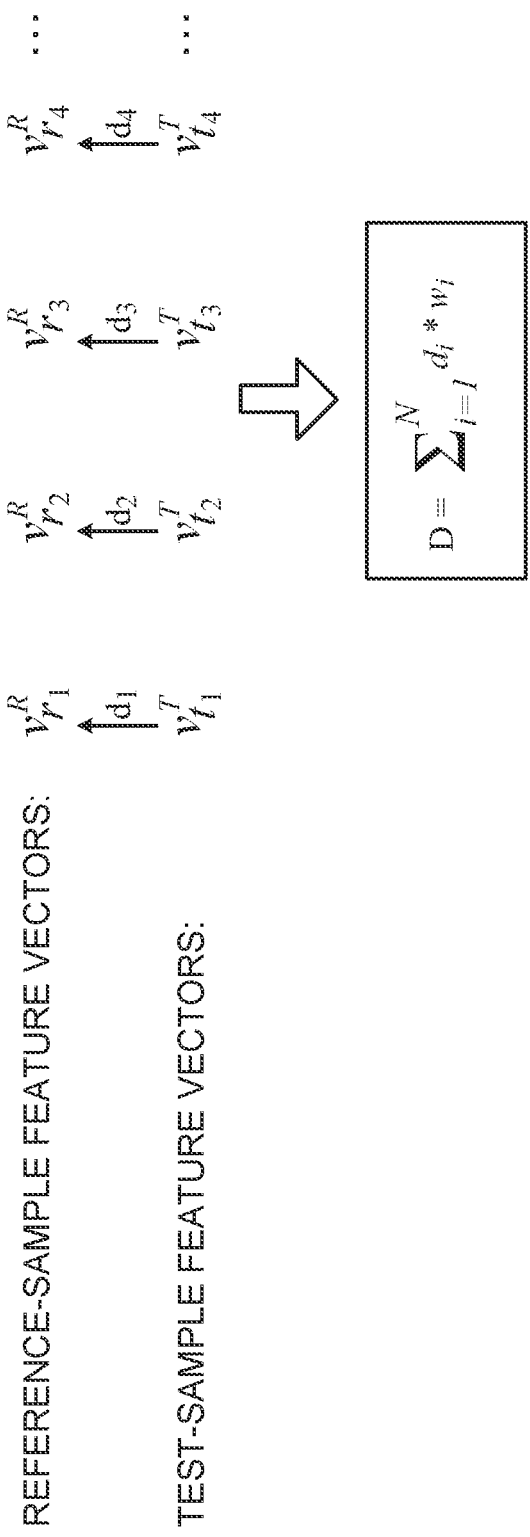
FIG. 5 is a schematic illustration of a mapping of a test speech sample to a reference speech sample, in accordance with some embodiments of the present invention.

For further details regarding this mapping, reference is now made to FIG. 5, which is a schematic illustration of a mapping of a test speech sample to a reference speech sample, in accordance with some embodiments of the present invention.

By way of introduction, it is noted that any mapping of the test sample to the reference sample—also referred to as an "alignment" of the test sample with the reference sample—may be represented by a sequence of N pairs of indices $\{(t_1,r_1), \ldots, (t_N,r_N)\}$, where each index $t_i$ is the index of a feature vector in the test sample, each index $r_i$ is the index of a feature vector in the reference sample, and hence, each pair of indices $(t_i, r_i)$ represents a correspondence between a test-sample feature vector and a reference-sample feature vector. For example, the correspondence between the tenth test-sample feature vector and the eleventh reference-sample feature vector is represented by the pair of indices (10,11).

Typically, the sequence of index-pairs must satisfy some predefined constraints for the alignment to be valid. Examples for such constraints include:

- Monotonicity and continuity: $t_i \leq t_{i+1}$, $r_i \leq r_{i+1}$, and $0 < (r_{i+1} + t_{i+1}) - (r_i + t_i) \leq 2$, for $i=1, \ldots, N-1$
- A constrained slope: $1 \leq t_{i+2} - t_i \leq 2$ and $1 \leq r_{i+2} - r_i \leq 2$, for $i=1, \ldots, N-2$
- Boundary conditions: $t_1=1$, $r_1=1$, $t_N=M$, and $r_N=L$, where the test sample includes M feature vectors and the reference sample includes L feature vectors Given any particular alignment, the total distance D between the test sample and the reference sample may be defined as $D=\sum_{i=1}^{N} d(v_{t_i}^T, v_{r_i}^R) w_i$, where $v_{t_i}^T$ is the $t_i^{th}$ feature vector of the test sample, $v_{r_i}^R$ is the $r_i^{th}$ feature vector of the reference sample, d is a local distance between the two feature vectors that may utilize any suitable distance measure (e.g., the L1 or L2 distance measure), and each $w_i$ is a weight that is applied to d. In some embodiments, $w_i=2$ and $w_i=(r_i+t_i)-(r_{i-1}+t_{i-1})$ for $i=2, \ldots, N$, such that the sum of the weights is M+L for each alignment, thus eliminating any a priori bias among the different alignments. Alternatively, the total distance D may be derived from the local distances in any other suitable way.

It is noted that in the context of the present application, including the claims, the "distance" between two vectors may be defined to include any sort of deviation, or distortion, of one of the vectors relative to the other. Thus, the local distance function does not necessarily return a distance in the geometric sense. For example, it may not be necessarily true that $d(v_{t_i}^T, v_{r_i}^R) = d(v_{r_i}^R, v_{t_i}^T)$, and/or it may not be necessarily true that for any three feature vectors $v_1$, $v_2$, and $v_3$, $d(v_1, v_3) \leq d(v_1, v_2) + d(v_2, v_3)$. An example of a non-geometric distance measure that may be used in embodiments of the present invention is the Itakura-Saito distance measure between vectors of linear-prediction (LPC) coefficients, which is described in section 4.5.4 of the aforementioned reference to Rabiner and Juang, which is incorporated herein by reference.

Further to the above introduction, FIG. 5 illustrates an alignment of the test sample with the reference sample, which may be performed by the processor, for example, using the dynamic time warping (DTW) algorithm, which is described in the aforementioned reference to Sakoe and Chiba, which is incorporated herein by reference. In particular, FIG. 5 shows a correspondence, between some of the test-sample features vectors and corresponding ones of the reference-sample feature vectors, resulting from the alignment. Each pair of corresponding feature vectors has an associated local distance $d_i$, where $d_i = d(v_{t_i}^T, v_{r_i}^R)$. From among all possible alignments, the processor selects the alignment that minimizes the distance D, e.g., using a dynamic programming algorithm described in section 4.7 of the aforementioned reference to Rabiner and Juang, which is incorporated herein by reference. (It is noted that the DTW algorithm includes a dynamic programming algorithm for finding the optimal alignment.)

(To avoid any confusion, it is noted that the four reference-sample feature vectors shown in FIG. 5 are not necessarily the first four feature vectors belonging to the reference sample. For example, $r_2$ may be 2 and $r_3$ may be 4, such that the third reference-sample feature vector is not mapped to. Similarly, the four test-sample feature vectors shown in FIG. 5 are not necessarily the first four feature vectors belonging to the test sample.)

In response to mapping the test speech sample to the reference speech sample, the processor may generate an output indicating the physiological state of the subject at the time at which the test speech sample was acquired. For example, the processor may compare the total distance D to a suitable predefined threshold, and generate an output in response to the comparison.

In some embodiments, as described above with reference to FIG. 2, the reference speech sample is produced while the physiological state of the subject is deemed to be stable with respect to a particular physiological condition. In other embodiments, the reference speech sample is produced while the physiological state of the subject is deemed to be unstable. In yet other embodiments, the processor receives two reference speech samples: a stable-state speech sample, and an unstable-state speech sample. The processor then maps the test sample to each of the reference speech samples, thus yielding a first distance to the stable-state speech sample, and a second distance to the unstable-state speech sample. The processor then compares the two distances to one another, and generates an output responsively thereto. For example, if the second distance is less than the first distance, indicating that the test sample is more similar to the unstable-state reference sample, the processor may generate an alert.

In some embodiments, the reference speech sample and the test speech sample include the same predetermined utterance, as described above with reference to FIG. 3. In other embodiments, the reference speech sample includes free speech of the subject, and the test speech sample includes a plurality of speech units that are included in the free speech. For example, using the techniques described above with reference to FIG. 4, the processor may identify multiple different speech units in the free speech of the subject. The processor may then construct an utterance from these speech units, and then prompt the subject to produce the test sample by uttering the utterance.

In some embodiments, the system computes multiple distances, with respect to different respective reference samples, for respective test samples; the system may then generate an alert responsively to the multiple distances, e.g., in response to one or more of the distances exceeding a threshold.

Using a Different Total Distance for the Diagnosis

In some embodiments, the processor, subsequently to performing the mapping of the test sample to the reference sample, computes another, different total distance between the test-sample feature vectors and the reference-sample feature vectors to which they are mapped. The processor then generates an output responsively to this other total distance.

For example, the processor may first select the mapping that minimizes $\Sigma_{i=1}^{N} d(v_{t_i}^T, v_{r_i}^R) w_i$, as described above. Subsequently, the processor may (without changing the mapping) compute $\Sigma_{i=1}^{N} d(v_{t_i}^T, v_{r_i}^R) u_i$, where at least one of the new weights $u_i$ is different from the corresponding original weight $w_i$. In other words, the processor may compute another weighted sum of the local distances in which the local distances are weighted by a new set of weights $\{u_i\}$ that differs from the original set of weights $\{w_i\}$ in that, for at least one index i, $u_i$ is different from $w_i$.

Typically, the new weights are selected by associating the reference-sample feature vectors with respective APUs, and then selecting the new weights responsively to the APUs. (In this context, a vector is said to be associated with an APU by the processor if the processor considers the vector to have been extracted from speech that is included in the APU.) For example, in response to $v_{r_2}^R$ and $v_{r_3}^R$ being associated with a particular APU that is known to be more relevant than other APUs to the subject's physiological condition, the processor may assign a higher value to $u_2$ and $u_3$, relative to the other new weights.

To associate the reference-sample features vectors with respective APUs, the processor may apply any suitable speech-recognition algorithm to the reference speech sample. For example, the processor may use any of the algorithms for speaker-independent, large-vocabulary connected speech recognition described in chapters 7-8 of the aforementioned reference to Rabiner and Juang, such as the One Stage Dynamic Programming algorithm.

Alternatively or additionally, in computing the new total distance, the processor may (without changing the mapping) use different local distances. In other words, the processor may compute the new total distance as $\Sigma_{i=1}^{N} d'(v_{t_i}^T, v_{r_i}^R) w_i$ (or $\Sigma_{i=1}^{N} d'(v_{t_i}^T, v_{r_i}^R) u_i$), where d' is a local distance function that is different from the original function, such that at least one of the new local distances differs from the corresponding original local distance, i.e., $d'(v_{t_i}^T, v_{r_i}^R)$ is different from $d(v_{t_i}^T, v_{r_i}^R)$ for at least one index i.

For example, for the new local distances, the processor may use a new distance measure that is different from the original distance measure. (For example, the processor may use the L1 distance measure instead of the L2 distance measure.) Alternatively or additionally, the processor may compute the new local distances based on at least one acoustic feature that did not contribute to the first local distances. For example, if the original local distance does not depend on the respective third elements of the vectors (which may quantify any particular acoustic feature), the processor may modify the local distance function such that the output of the function depends on these elements.

Example Algorithm

Figure 6:
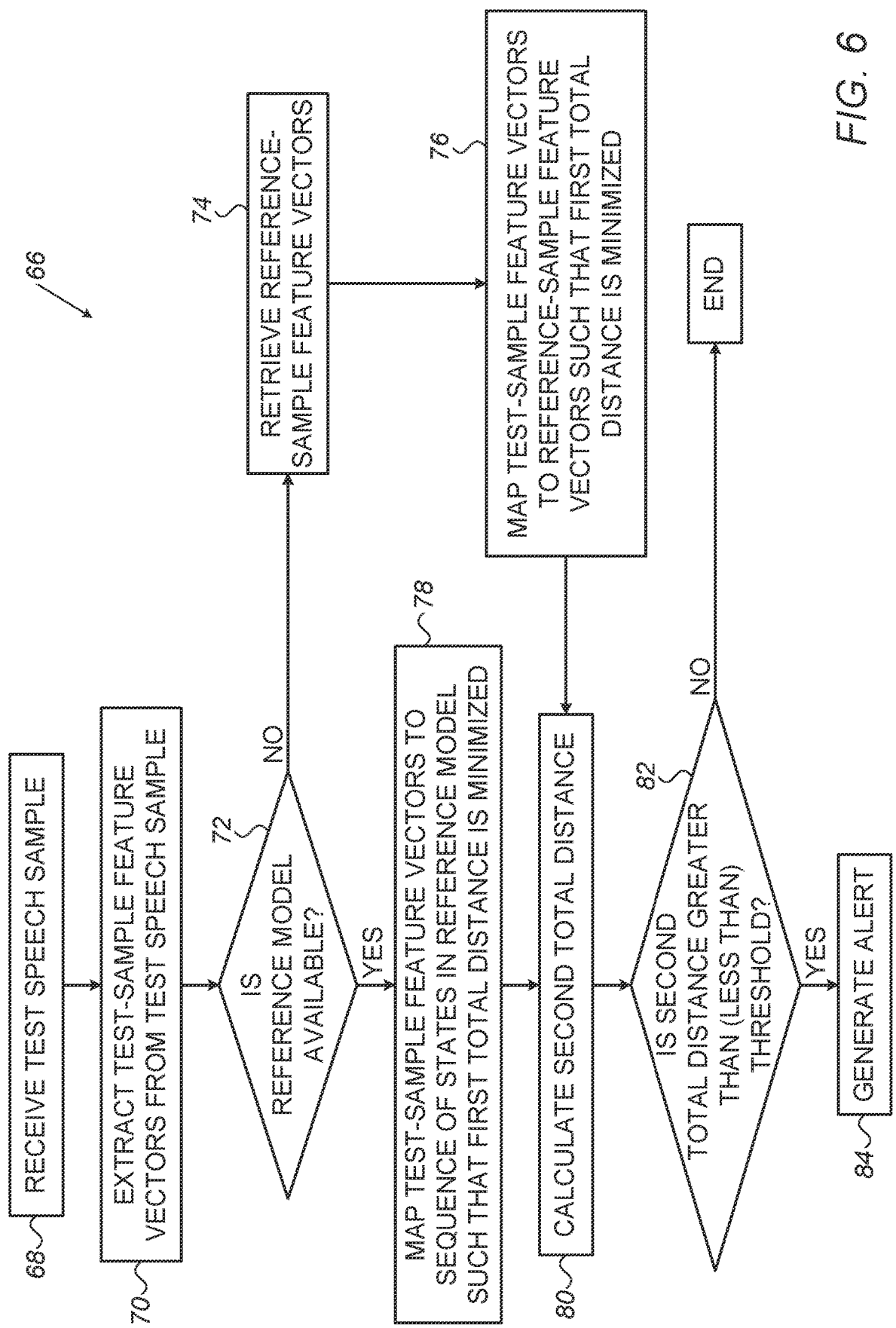
FIG. 6 is a flow diagram for an example algorithm for evaluating a test speech sample of a subject, in accordance with some embodiments of the present invention.

Reference is now made to FIG. 6, which is a flow diagram for an example algorithm 66 for evaluating a test speech sample of a subject, in accordance with some embodiments of the present invention.

Algorithm 66 begins at a receiving step 68, at which the processor receives a test speech sample from the subject. Following the receipt of the sample, the processor extracts test-sample feature vectors from the sample, at an extracting step 70. Next, the processor checks, at a checking step 72, whether a suitable reference model is available. (As noted above with reference to FIG. 4, such a model may be constructed from reference samples that were received from the subject, and/or from reference samples that were received from multiple other subjects.) For example, the processor may look for a suitable model by querying a database that is stored in memory 30 (FIG. 1).

Subsequently, if the processor is able to find a suitable reference model, the processor, at a first mapping step 78, maps the test-sample feature vectors to a sequence of states in the reference model such that a first total distance between the vectors and the states is minimized, as described above with reference to FIG. 3. Alternatively, if the processor is unable to find a suitable reference model, the processor, at a retrieving step 74, retrieves a sequence of reference-sample feature vectors, which were previously extracted from a reference sample of the subject. Subsequently, at a second mapping step 76, the processor maps the test-sample feature vectors to the reference-sample feature vectors such a first total distance between the sequences of vectors is minimized, as described above with reference to FIG. 5.

Following first mapping step 78 or second mapping step 76, the processor, at a distance-calculating step 80, calculates a second total distance between (i) the test-sample feature vectors and (ii) the reference model or the reference-sample feature vectors. For example, as described above with reference to FIGS. 4-5, the processor may, in computing the second total distance, change the relative weightings of the local distances, and/or change the local distances themselves.

Subsequently, at a comparing step 82, the processor compares the second total distance to a threshold. If the second total distance is greater than (or, in some cases, such as where the reference samples correspond to an unstable state, less than) the threshold, the processor generates an alert, at an alert-generating step 84. Otherwise, algorithm 66 may terminate without any further activity; alternatively, the processor may generate an output indicating that the subject's state is stable.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
    obtaining a first sequence of reference-sample feature vectors that quantify acoustic features of different respective portions of at least one reference speech sample, which was produced by a subject at a first time while a physiological state of the subject was known;
    obtaining a second sequence of test-sample feature vectors that quantify the acoustic features of different respective portions of at least one test speech sample, which was produced by the subject at a second time while the physiological state of the subject was unknown;
    aligning the test speech sample with the reference speech sample, by mapping the test-sample feature vectors to respective ones of the reference-sample feature vectors, under predefined constraints, such that a total distance between the second sequence and the first sequence is minimized; and
    in response to aligning the test speech sample with the reference speech sample, generating an output indicating the physiological state of the subject at the second time.

2. The method according to claim 1, further comprising receiving the test speech sample, wherein obtaining the test-sample feature vectors comprises obtaining the test-sample feature vectors by computing the test-sample feature vectors based on the test speech sample.

3. The method according to claim 1, wherein the total distance is derived from respective local distances between the test-sample feature vectors and the respective ones of the reference-sample feature vectors.

4. The method according to claim 3, wherein the total distance is a weighted sum of the local distances.

5. The method according to claim 4, wherein aligning the test speech sample with the reference speech sample comprises aligning the test speech sample with the reference speech sample using a dynamic time warping (DTW) algorithm.

6. The method according to claim 1, wherein generating the output comprises:
    comparing the total distance to a predetermined threshold; and
    generating the output in response to the comparison.

7. The method according to claim 1, wherein the reference speech sample was produced while the physiological state of the subject was stable with respect to a particular physiological condition.

8. The method according to claim 1, wherein the reference speech sample was produced while the physiological state of the subject was unstable with respect to a particular physiological condition.

9. The method according to claim 1, wherein the reference speech sample and the test speech sample include the same predetermined utterance.

10. The method according to claim 1, wherein the reference speech sample includes free speech of the subject, and wherein the test speech sample includes a plurality of speech units that are included in the free speech.

11. Apparatus, comprising:
    a network interface; and
    a processor, configured to:
        obtain a first sequence of reference-sample feature vectors that quantify acoustic features of different respective portions of at least one reference speech sample, which was produced by a subject at a first time while a physiological state of the subject was known,
        obtain, via the network interface, a second sequence of test-sample feature vectors that quantify the acoustic features of different respective portions of at least one test speech sample, which was produced by the subject at a second time while the physiological state of the subject was unknown,
        align the test speech sample with the reference speech sample, by mapping the test-sample feature vectors to respective ones of the reference-sample feature vectors, under predefined constraints, such that a total distance between the second sequence and the first sequence is minimized, and
        in response to aligning the test speech sample with the reference speech sample, generate an output indicating the physiological state of the subject at the second time.

12. The apparatus according to claim 11, wherein the processor is configured to obtain the second sequence by:
    receiving the test speech sample, and
    computing the test-sample feature vectors based on the test speech sample.

13. The apparatus according to claim 11, wherein the total distance is derived from respective local distances between the test-sample feature vectors and the respective ones of the reference-sample feature vectors.

14. The apparatus according to claim 11, wherein the processor is configured to generate the output by:
    comparing the total distance to a predetermined threshold, and
    generating the output in response to the comparison.

15. The apparatus according to claim 11, wherein the reference speech sample was produced while the physiological state of the subject was stable with respect to a particular physiological condition.

16. A system, comprising:
    an analog-to-digital (A/D) converter; and
    one or more processors, configured to cooperatively carry out a process that includes:
        obtaining a first sequence of reference-sample feature vectors that quantify acoustic features of different respective portions of at least one reference speech sample, which was produced by a subject at a first time while a physiological state of the subject was known,
        receiving, via the A/D converter, at least one test speech sample that was produced by the subject at a second time while the physiological state of the subject was unknown,
        computing a second sequence of test-sample feature vectors that quantify the acoustic features of different respective portions of the test speech sample,
        aligning the test speech sample with the reference speech sample, by mapping the test-sample feature vectors to respective ones of the reference-sample feature vectors, under predefined constraints, such that a total distance between the second sequence and the first sequence is minimized, and in response to aligning the test speech sample with the reference speech sample, generating an output indicating the physiological state of the subject at the second time.

17. The system according to claim 16, wherein the process further includes receiving the reference speech sample, and wherein obtaining the first sequence of reference-sample feature vectors includes obtaining the first sequence of reference-sample feature vectors by computing the reference-sample feature vectors based on the reference speech sample.

18. The system according to claim 16, wherein the reference speech sample and the test speech sample include the same predetermined utterance.

19. A computer software product comprising a tangible non-transitory computer-readable medium in which program instructions are stored, which instructions, when read by a processor, cause the processor to:

obtain a first sequence of reference-sample feature vectors that quantify acoustic features of different respective portions of at least one reference speech sample, which was produced by a subject at a first time while a physiological state of the subject was known, obtain a second sequence of test-sample feature vectors that quantify the acoustic features of different respective portions of at least one test speech sample, which was produced by the subject at a second time while the physiological state of the subject was unknown, align the test speech sample with the reference speech sample, by mapping the test-sample feature vectors to respective ones of the reference-sample feature vectors, under predefined constraints, such that a total distance between the second sequence and the first sequence is minimized, and in response to aligning the test speech sample with the reference speech sample, generate an output indicating the physiological state of the subject at the second time.

20. The computer software product according to claim 19, wherein the instructions further cause the processor to receive the test speech sample, and wherein the instructions cause the processor to obtain the second sequence of test-sample feature vectors by computing the test-sample feature vectors based on the test speech sample.

\* \* \* \* \*